US011406578B2

(12) United States Patent
Deconinck et al.

(10) Patent No.: US 11,406,578 B2
(45) Date of Patent: Aug. 9, 2022

(54) PROCESS FOR STRIPPING KERATIN FIBRES USING A COMPOSITION COMPRISING A SULFINIC ACID DERIVATIVE AND AN ACIDIC AQUEOUS COMPOSITION

(75) Inventors: Gautier Deconinck, Saint Gratien (FR); Laure Jouffroy-Wendlinger, Saint-Arnoult-en-Yvelines (FR); Sylvain Kravtchenko, Asnieres (FR); Damarys Braida-Valerio, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 13/989,438

(22) PCT Filed: Nov. 24, 2011

(86) PCT No.: PCT/EP2011/070963
§ 371 (c)(1),
(2), (4) Date: Jun. 27, 2013

(87) PCT Pub. No.: WO2012/069599
PCT Pub. Date: May 31, 2012

(65) Prior Publication Data
US 2013/0266529 A1    Oct. 10, 2013

Related U.S. Application Data

(60) Provisional application No. 61/420,513, filed on Dec. 7, 2010, provisional application No. 61/420,517, filed on Dec. 7, 2010, provisional application No. 61/420,511, filed on Dec. 7, 2010.

(30) Foreign Application Priority Data

Nov. 25, 2010   (FR) ........................ 1059711
Nov. 25, 2010   (FR) ........................ 1059713
Nov. 25, 2010   (FR) ........................ 1059714

(51) Int. Cl.
*A61K 8/46*       (2006.01)
*A61Q 5/08*       (2006.01)
*A61K 8/365*      (2006.01)

(52) U.S. Cl.
CPC ............... *A61K 8/46* (2013.01); *A61K 8/365* (2013.01); *A61Q 5/08* (2013.01)

(58) Field of Classification Search
None
See application file for complete search history.

(56) References Cited

U.S. PATENT DOCUMENTS

| | | |
|---|---|---|
| 2,149,319 A | 3/1939 | Soussa |
| 2,798,053 A | 7/1957 | Brown |
| 2,923,692 A | 2/1960 | Ackerman et al. |
| 3,148,125 A | 9/1964 | Strianse et al. |
| 3,190,803 A | 6/1965 | Vogt |
| 3,645,705 A | 2/1972 | Miller et al. |
| 3,838,966 A | 10/1974 | Barchas et al. |
| 3,892,845 A | 7/1975 | Cunningham et al. |
| 3,915,921 A | 10/1975 | Schlatzer, Jr. |
| 3,969,087 A | 7/1976 | Saito et al. |
| 4,003,699 A | 1/1977 | Rose et al. |
| RE30,199 E | 1/1980 | Rose et al. |
| 4,237,243 A | 12/1980 | Quack et al. |
| 4,509,949 A | 4/1985 | Huang et al. |
| 5,061,289 A | 10/1991 | Clausen et al. |

(Continued)

FOREIGN PATENT DOCUMENTS

| | | |
|---|---|---|
| DE | 1151242 | 7/1963 |
| DE | 2359399 | 6/1975 |

(Continued)

OTHER PUBLICATIONS

English translation of FR 2814948.*

(Continued)

*Primary Examiner* — Patricia Duffy
*Assistant Examiner* — Garen Gotfredson
(74) *Attorney, Agent, or Firm* — The Marbury Law Group, PLLC

(57) ABSTRACT

The present invention relates to a process for stripping keratin fibres, and in particular human keratin fibres such as the hair, dyed with oxidation dyes and/or direct dyes, using a composition obtained by extemporaneous mixing of an anhydrous or aqueous composition (A) comprising at least one suitably selected sulfinic acid derivative and an aqueous composition (B) with a pH of less than (5), comprising at least one organic acid other than the compounds of formula (I), with a pKa of less than or equal to (4) when the composition (A) is aqueous, the pH of the mixture of the two compositions (A) and (B) being less than or equal to (5). The invention also relates to a composition for stripping the artificial colour from keratin fibres, comprising at least one suitably selected sulfinic acid derivative and at least one thickener chosen from anionic polymers and nonionic polymers. The compositions used in the context of the invention afford efficient stripping, especially in terms of power, of the artificial colour of keratin fibres dyed with a wide range of oxidation dyes and/or direct dyes. They do not induce lightening of the natural base of the keratin fibres and limit the sensitization of the keratin fibres. They apply well to the hair, uniformly, which makes it possible to obtain regular stripping of the colour along the entire fibre.

23 Claims, No Drawings

(56) References Cited

U.S. PATENT DOCUMENTS

| | | |
|---|---|---|
| 5,089,578 A | 2/1992 | Valint et al. |
| 5,156,911 A | 10/1992 | Stewart |
| 5,380,340 A | 1/1995 | Neunhoeffer et al. |
| 5,468,477 A | 11/1995 | Kumar et al. |
| 5,500,209 A | 3/1996 | Ross et al. |
| 5,519,063 A | 5/1996 | Mondet et al. |
| 5,534,267 A | 7/1996 | Neunhoeffer et al. |
| 5,663,366 A | 9/1997 | Neunhoeffer et al. |
| 5,708,151 A | 1/1998 | Mockli |
| 5,725,882 A | 3/1998 | Kumar et al. |
| 5,736,125 A | 4/1998 | Morawsky et al. |
| 5,766,576 A | 6/1998 | Lowe et al. |
| 5,783,657 A | 7/1998 | Pavlin et al. |
| 6,099,592 A | 8/2000 | Vidal et al. |
| 6,099,593 A | 8/2000 | Terranova et al. |
| 6,106,579 A | 8/2000 | Kunz et al. |
| 6,120,780 A | 9/2000 | Dupuis et al. |
| 6,174,968 B1 | 1/2001 | Hoxmeier |
| 6,211,400 B1 | 4/2001 | Berghofer et al. |
| 6,225,390 B1 | 5/2001 | Hoxmeier |
| 6,225,690 B1 | 5/2001 | Juneja et al. |
| 6,284,003 B1 | 9/2001 | Rose et al. |
| 6,338,741 B1 | 1/2002 | Vidal et al. |
| 6,379,657 B1 | 4/2002 | Lorenz et al. |
| 6,645,258 B2 | 11/2003 | Vidal et al. |
| 6,822,039 B1 | 11/2004 | Monfreux-Gaillard et al. |
| 2002/0050013 A1 | 5/2002 | Vidal et al. |
| 2003/0019051 A9 | 1/2003 | Vidal et al. |
| 2004/0034944 A1 | 2/2004 | Legrand et al. |
| 2005/0008589 A1 | 1/2005 | Legrand et al. |
| 2005/0132505 A9 | 6/2005 | Legrand et al. |
| 2005/0191251 A1* | 9/2005 | Kravtchenko et al. ......... 424/62 |
| 2005/0251928 A1 | 11/2005 | Kravtchenko et al. |
| 2008/0085249 A1* | 4/2008 | Cannell et al. ................ 424/62 |

FOREIGN PATENT DOCUMENTS

| | | |
|---|---|---|
| DE | 3843892 | 6/1990 |
| DE | 4133957 | 4/1993 |
| DE | 19543988 | 5/1997 |
| EP | 0173109 | 3/1986 |
| EP | 0216479 | 4/1987 |
| EP | 0497144 | 8/1992 |
| EP | 0503853 | 9/1992 |
| EP | 0714954 | 10/1995 |
| EP | 0750899 | 1/1997 |
| EP | 0815828 | 1/1998 |
| EP | 0943316 | 9/1999 |
| EP | 1086685 | 3/2001 |
| EP | 1598053 | 11/2005 |
| FR | 2281162 | 3/1976 |
| FR | 2416723 | 9/1979 |
| FR | 2733749 | 11/1996 |
| FR | 2750048 | 12/1997 |
| GB | 1026978 | 4/1966 |
| GB | 1153196 | 5/1969 |
| JP | H0219576 | 1/1990 |
| JP | H04245241 | 9/1992 |
| JP | 2004356413 | 12/2004 |
| WO | 93/01797 | 2/1993 |
| WO | 94/08969 | 4/1994 |
| WO | 94/08970 | 4/1994 |
| WO | 95/01772 | 1/1995 |
| WO | 95/15144 | 6/1995 |
| WO | 96/15765 | 5/1996 |
| WO | 98/42298 | 3/1997 |
| WO | 00/31154 | 6/2000 |
| WO | 01/19333 | 3/2001 |
| WO | 02/15855 | 2/2002 |
| WO | 02/15855 A1 | 2/2002 |
| WO | 02/30369 | 4/2002 |
| WO | 02/30369 A1 | 4/2002 |
| WO | 2007/107310 | 9/2007 |
| WO | 2007/107310 A2 | 9/2007 |

OTHER PUBLICATIONS

International Search Report for PCT/EP2011/070963 (dated 2013).
English language abstract for JPH0219576 (1990).
English language abstract for JPH04245241 (1992).
English language abstract for JP2004356413 (2004).
Boutevin, B., et al., "Study of Morphological and Mechanical Properties of PP/PBT," Polymer Bulletin, 34, 1995, pp. 117-123.
Hamley, I.W., "Crystallization in Block Copolymers," Advances in Polymer Science, vol. 148, 1999, pp. 113-137.
Nojima, S., "Melting Behaviour of Poly(δ-caprolactone)-block-polybutadiene Copolymers," Macromolecules, 32, 1999, pp. 3727-3734.
Rangarajan, P., et al., "Morphology of Semi-Crystalline Block Copolymers of Ethylene-(ethylene-alt-propylene)," Macromolecules, 26, 1993, pp. 4640-4645.
Richter, P., et al., "Polymer Aggregates with Crystalline Cores: the System Poly(ethylene)poly(ethylene-propylene)," Macromolecules, 30, 1997, pp. 1053-1068.
European Search Report for counterpart EP Application No. 18213760, dated Sep. 6, 2019.

* cited by examiner

PROCESS FOR STRIPPING KERATIN FIBRES USING A COMPOSITION COMPRISING A SULFINIC ACID DERIVATIVE AND AN ACIDIC AQUEOUS COMPOSITION

This is a national stage application of PCT/EP2011/070963, filed internationally on Nov. 24, 2011, which claims priority to U.S. Provisional Application No. 61/420,513, filed on Dec. 7, 2010; 61/420,517, filed on Dec. 7, 2010, and 61/420,511, filed Dec. 7, 2010, as well as French Application Nos. FR 1059711, filed on Nov. 25, 2010; FR 1059713, filed on Nov. 25, 2010 and FR 1059714, filed on Nov. 25, 2010.

The present invention relates to a process for stripping keratin fibres, and in particular human keratin fibres such as the hair, dyed with oxidation dyes and/or direct dyes, using a composition obtained by extemporaneous mixing of an anhydrous or aqueous composition (A) comprising at least one suitably selected sulfinic acid derivative and an aqueous composition (B) with a pH of less than 5, optionally comprising at least one organic acid with a pKa of less than or equal to 4, the pH of the mixture of the two compositions (A) and (B) being less than or equal to 5.

It is known practice to dye keratin fibres, and in particular human keratin fibres such as the hair, with dye compositions containing oxidation dyes and/or direct dyes.

The dyeing performed with oxidation dyes, or "oxidation dyeing", is permanent dyeing; it comprises, as oxidation dyes, oxidation dye precursors and couplers.

Oxidation dye precursors, commonly known as "oxidation bases" are compounds that are initially colourless or weakly coloured, which develop their dyeing power within the hair in the presence of oxidizing agents added at the time of use, leading to the formation of coloured and colouring compounds. The formation of these coloured and colouring compounds results either from an oxidative condensation of the "oxidation bases" with themselves, or from an oxidative condensation of the "oxidation bases" with coloration modifiers, commonly known as "couplers", which are generally present in the dye compositions used in oxidation dyeing.

The variety of molecules used as oxidation bases and couplers allows a wide range of colours to be obtained.

The dyeing performed with direct dyes gives semi-permanent or temporary coloration; direct dyes give the natural coloration of the hair a more or less pronounced colour change that may withstand shampoo washing several times.

The direct dyes conventionally used are chosen especially from nitrobenzene direct dyes, azo direct dyes, quinone and in particular anthraquinone direct dyes, azine direct dyes, triarylmethane direct dyes, indoamine direct dyes and natural direct dyes.

To vary the shades obtained in oxidation dyeing, or to enrich them with tints, oxidation dyes may be used in combination with direct dyes.

For various reasons, such as the wish to partially or totally modify the shade thus given to the head of hair by oxidation dyeing or direct dyeing, or the wish to remove this coloration, the user may be led to partially or totally destroy the dyes thus formed or introduced into or onto the hair. Stripping of the artificial colour of the keratin fibres is then performed.

This stripping is generally performed via processes using oxidizing or reducing systems.

In oxidizing systems, the oxidizing agents conventionally used are hydrogen peroxide or compounds that are capable of producing peroxygenated compounds by hydrolysis.

Among the reducing systems, on the one hand, German patent DE 1 151 242 discloses the use of hydroxymethanesulfinic acid at a pH of between 7 and 9, for bleaching coloured hair. The use of sodium sulfite ($Na_2SO_3$) is also disclosed in patents U.S. Pat. Nos. 2,149,319 and 3,838,966 and patent application JP-04356413A.

It is also known practice to strip keratin fibres using reducing agents at acidic pH. Thus, it is known practice to use sodium hydroxymethanesulfinate as a reducing agent for dyed hair, which is mixed at the time of the use with an acidic aqueous solution. Patent application EP 0 943 316 discloses the use of a combination at acidic pH comprising ascorbic acid and α-oxocarboxylic acid, for stripping the hair.

A process for stripping the artificial colour of keratin fibres is also described in patent U.S. Pat. No. 3,892,845 and consists in applying to the fibres an aqueous composition comprising a combination of two types of reducing agent, a reducing agent for the dye and a reducing agent for the disulfide covalent bonds of keratin; the reducing agent for the dye is a zinc, potassium, sodium or calcium hydroxymethanesulfinate or hydrosulfite, and the reducing agent for keratin is especially thioglycolic acid, a potassium or sodium bisulfate or bisulfite, potassium disulfide, thiourea or certain phosphorus compounds, such as phosphines.

Finally, patent EP 1 326 576 proposes the use, for stripping keratin fibres dyed with oxidation dyes and/or direct dyes, of a cosmetic composition with a pH of between 1.5 and 9, comprising at least one suitably selected sulfinic acid derivative.

However, all these prior art techniques do not give rise to sufficiently efficient stripping of the keratin fibres, in particular in the case of oxidation dyeing, and most particularly for fundamental shades and shades with golden and ash-coloured tints.

Moreover, the results obtained may be very variable from one type of fibre to another, in particular for fibres of the same nature but having variable degrees of sensitization as a function of the various treatments undergone.

The aim of the present invention is to provide compositions for stripping the artificial colour of keratin fibres, which do not have the drawbacks of the stripping products known in the prior art, in particular more efficient compositions for stripping the artificial colour of keratin fibres.

This aim is achieved with the present invention, one subject of which is a process for stripping keratin fibres, and in particular human keratin fibres such as the hair, dyed with oxidation dyes and/or direct dyes, using a composition obtained by extemporaneous mixing of:

(a) an anhydrous or aqueous composition (A) comprising at least one sulfinic acid derivative of formula (I) below, and also the cosmetically acceptable salts thereof:

(I)

in which:

$R_1$ is chosen from a hydrogen atom, an ion $NH_3^+$, a monovalent metal ion or an ionic equivalent of a divalent metal from groups Ia, IIa, IIb, IVa and VIIIb of the Periodic Table of the Elements;

$R_2$ is chosen from a radical OH, a radical $NR_5R_6$ in which $R_5$ and $R_6$, which may be identical or different, are chosen from a hydrogen atom and a $C_1$-$C_6$ alkyl radical;

$R_3$ is chosen from a hydrogen atom, an alkyl or alkenyl or cycloalkyl or aryl radical which is unsubstituted or substituted with 1 to 3 substituents, which may be identical or different, chosen from OH, $C_1$-$C_6$ alkyl, $C_1$-$C_6$ O-alkyl, halogen and $CF_3$ radicals;

$R_4$ is chosen from a radical $COOR_5$, $SO_3R_1$, $COR_5$, $CONR_5R_6$ or $COOR_5$ in which $R_1$, $R_5$ and $R_6$ have the preceding meanings;

$R_4$ also denotes a hydrogen atom when $R_3$ denotes an aryl radical, and in particular an aryl radical substituted as described previously;

with (b) an aqueous composition (B) with a pH of less than 5; the said composition (B) comprising at least one organic acid different from the compounds of formula (I) and with a pKa of less than or equal to 4 when composition (A) is aqueous; the pH of the mixture of the two compositions (A) and (B) being less than or equal to 5.

A subject of the present invention is also the use, for the stripping of keratin fibres dyed with oxidation dyes and/or direct dyes, of a composition obtained by extemporaneous mixing of an anhydrous or aqueous composition (A) comprising at least one sulfinic acid derivative of formula (I) as defined previously and of an aqueous composition (B) with a pH of less than 5, the said composition (B) comprising, when composition (A) is aqueous, at least one organic acid other than the compounds of formula (I) and with a pKa of less than or equal to 4, the pH of the mixture of the two compositions (A) and (B) being less than or equal to 5.

A subject of the present invention is also a multi-compartment device for stripping the artificial colour of keratin fibres dyed with oxidation dyes and/or direct dyes.

Similarly, a subject of the present invention is a composition for stripping keratin fibres dyed with oxidation dyes and/or direct dyes, comprising, in a cosmetically acceptable medium, at least one sulfinic acid derivative of formula (I) and cosmetically acceptable salts thereof, as defined previously; and at least one thickener chosen from anionic polymers and nonionic polymers.

The invention also relates to a process for stripping keratin fibres dyed with oxidation dyes and/or direct dyes, in which such a composition is applied to the keratin fibres for a leave-on time that is sufficient to strip the artificial colour from the keratin fibres; and also to the use of this composition for stripping keratin fibres dyed with oxidation dyes and/or direct dyes.

A final subject of the invention is formed by a multi-compartment device for dyeing and then stripping the artificial colour of keratin fibres, comprising a first compartment containing a composition comprising at least one oxidation dye precursor and/or at least one direct dye; a second compartment containing a stripping composition comprising at least one sulfinic acid derivative of the abovementioned formula (I), or salts thereof, and at least one thickener chosen from anionic polymers and nonionic polymers; and optionally a third compartment containing an oxidizing composition.

The composition according to the present invention affords efficient stripping, especially in terms of power, of the artificial colour of keratin fibres dyed with a wide range of oxidation dyes and/or direct dyes. It does not induce lightening of the natural base of the keratin fibres and limits the sensitization of the keratin fibres. It also affords stripping that is relatively insensitive to the differences in sensitization between keratin fibres.

It applies well to the hair, uniformly, which makes it possible to obtain regular stripping of the colour along the entire fibre.

In the context of the present invention, the term "at least one" is equivalent to "one or more".

Unless otherwise indicated, the limits of the ranges of values that are given in the context of the present invention are included in these ranges.

For the purposes of the invention, a composition is anhydrous when it has a water content of less than 1% by weight and preferably less than 0.5% by weight relative to the total weight of the composition.

For the purposes of the present invention, an aqueous composition comprises more than 5% by weight of water, preferably more than 10% by weight of water and even more advantageously more than 20% by weight of water.

The cosmetically acceptable salts of the sulfinic acid derivatives of formula (I) that are useful in the context of the invention may be chosen from alkali metal (Na, K), alkaline-earth metal (Ca, Mg) or zinc sulfinates.

The sulfinic acid derivatives of formula (I) according to the invention are known compounds, which are described and prepared in patent application WO 99/18067.

The sulfinic acid(s) and/or salts thereof may be present in the composition derived from the mixing of compositions (A) and (B) in proportions ranging from 0.01% to 20% and preferably from 0.1% to 10% by weight relative to the total weight of the composition.

According to one particular embodiment of the invention, the sulfinic acid derivative(s) of formula (I) are such that:

$R_1$ is chosen from an ion $NH_3^+$, an alkali metal ion, and an ionic equivalent of an alkaline-earth metal or of zinc;

$R_2$ is a radical OH or a radical $NH_2$;

$R_3$ is chosen from a hydrogen atom, an alkyl radical which is unsubstituted or substituted with one or two radicals OH or one or two $C_1$-$C_6$ alkyl or $C_1$-$C_6$ O-alkyl radicals;

$R_4$ is a radical $COOR_1$ or $COOR_5$, in which $R_1$ and $R_5$ have the same meanings as in formula (I).

According to another particular embodiment of the invention, the sulfinic acid derivative(s) of formula (I) are such that:

$R_1$ is chosen from an ion $NH_3^+$, an alkali metal ion, and an ionic equivalent of an alkaline-earth metal or of zinc;

$R_2$ is a radical OH;

$R_3$ is chosen from a hydrogen atom, an alkyl radical which is unsubstituted or substituted with one or two radicals OH or one or two $C_1$-$C_6$ alkyl or $C_1$-$C_6$ O-alkyl radicals;

$R_4$ is a radical $COOR_5$ or $COOR_5$, in which $R_1$ and $R_5$ have the same meanings as in formula (I).

Preferably, the compound of formula (I) is such that $R_1$ is Na, $R_2$ is OH, $R_3$ is H and $R_4$ is COONa, which corresponds to the compound of formula (II) below:

alone or as a mixture.

Mixtures comprising the compound of formula (II) comprise, for example, by weight, 20% to 60% of a compound of formula (II), 10% to 60% of $NaSO_3$—CHOH—COONa and 1% to 40% of $Na_2SO_3$.

One of these mixtures sold by the company Bruggemann under the trade name Brüggolite FF7 comprises, by weight, 32% of the compound $NaSO_2$—CHOH—COONa, 55% of the compound $NaSO_3$—CHOH—COONa and 3% of $Na_2SO_3$.

The anhydrous composition (A) that is useful in the context of the invention may also contain additional reducing agents other than the sulfinic acid derivatives of formula (I), such as those described in patent application EP 0 943 316. Mention may be made especially of sulfinates, sugars, reductones and α-oxocarboxylic acids such as oxalic acid, glyoxalic acid, pyruvic acid or α-ketoglutaric acid, and also the phosphines described in patent EP 1 598 053.

When the composition (A) that is useful in the context of the invention is anhydrous, it may furthermore comprise at least one inert organic liquid phase.

The term "inert phase" means a phase that does not lead to rapid destruction of the compounds of formula (I), i.e. more than 30% loss in 24 hours.

For the purposes of the present invention, the term "liquid phase" means any phase that is capable of flowing at room temperature, generally between 15° C. and 40° C., and at atmospheric pressure, under the action of its own weight.

Examples of inert liquid phases that may be mentioned include the polydecenes of formula $C_{10n}H_{[(20n)+2]}$ in which n ranges from 3 to 9 and preferably from 3 to 7, esters of fatty alcohols or of fatty acids, sugar esters or diesters of $C_{12}$-$C_{24}$ fatty acids, cyclic esters, cyclic ethers, silicone oils, mineral oils and plant oils, or mixtures thereof.

The compounds of formula $C_{10n}H_{[(20n)+2]}$ in which n ranges from 3 to 9 correspond to the name "polydecene" of the CTFA dictionary, 7th edition, 1997 of the Cosmetic, Toiletry and Fragrance Association, USA, and also to the same INCI name in the USA and in Europe. These are poly-1-decene hydrogenation products.

Among these compounds, those for which, in the formula, n ranges from 3 to 7 are preferred.

Examples that may be mentioned include the products sold under the name Silkflo® 366 NF Polydecene by the company Amoco Chemical, and those sold under the name Nexbase® 2002 FG, 2004 FG, 2006 FG and 2008 FG by the company Fortum.

As regards the esters of fatty alcohols or of fatty acids, examples that may be mentioned include:

- esters of saturated, linear or branched $C_3$-$C_6$ lower mono-alcohols with monofunctional $C_{12}$-$C_{24}$ fatty acids, these fatty acids possibly being linear or branched, saturated or unsaturated and chosen especially from oleates, laurates, palmitates, myristates, behenates, cocoates, stearates, linoleates, linolenates, caprates and arachidonates, or mixtures thereof, and especially oleo-palmitates, oleo-stearates and palmito-stearates. Among these esters, it is more particularly preferred to use isopropyl palmitate, isopropyl myristate and octyldodecyl stearate,
- esters of linear or branched $C_3$-$C_8$ monoalcohols with difunctional $C_8$-$C_{24}$ fatty acids, these fatty acids possibly being linear or branched, and saturated or unsaturated, for instance the isopropyl diester of sebacic acid, also known as diisopropyl sebacate,
- esters of linear or branched $C_3$-$C_8$ monoalcohols with difunctional $C_2$-$C_8$ fatty acids, these fatty acids possibly being linear or branched, and saturated or unsaturated, for instance dioctyl adipate and dicaprylyl maleate,
- the ester of a trifunctional acid, for instance triethyl citrate.

As regards the sugar esters and diesters of $C_{12}$-$C_{24}$ fatty acids, the term "sugar" means compounds containing several alcohol functions, with or without an aldehyde or ketone function, and which comprise at least 4 carbon atoms. These sugars may be monosaccharides, oligosaccharides or polysaccharides.

As sugars that may be used according to the invention, examples that may be mentioned include sucrose (or saccharose), glucose, galactose, ribose, fucose, maltose, fructose, mannose, arabinose, xylose and lactose, and derivatives thereof, especially alkyl derivatives such as methyl derivatives, for instance methylglucose.

The sugar esters of fatty acids that may be used according to the invention may be chosen especially from the group comprising esters or mixtures of esters of sugars described above and of linear or branched, saturated or unsaturated $C_{12}$-$C_{24}$ fatty acids.

The esters may be chosen from mono-, di-, tri-, tetraesters and polyesters, and mixtures thereof.

These esters may be chosen, for example, from oleates, laurates, palmitates, myristates, behenates, cocoates, stearates, linoleates, linolenates, caprates and arachidonates, or mixtures thereof such as, especially, oleo-palmitate, oleo-stearate and palmito-stearate mixed esters.

It is more particularly preferred to use monoesters and diesters and especially sucrose, glucose or methyl-glucose mono- or dioleates, stearates, behenates, oleopalmitates, linoleates, linolenates and oleo-stearates.

An example that may be mentioned is the product sold under the name Glucate® DO by the company Amerchol, which is a methylglucose dioleate.

Examples of esters or mixtures of esters of sugar and of fatty acid that may also be mentioned include:

- the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
- the products sold under the name Ryoto Sugar Esters, for example referenced B370 and corresponding to sucrose behenate formed from 20% monoester and 80% di-triester-polyester;
- the sucrose mono-dipalmito-stearate sold by the company Goldschmidt under the name Tegosoft® PSE.

As regards the cyclic ethers and cyclic esters, γ-butyrolactone, dimethyl isosorbide and diisopropyl isosorbide are especially suitable.

Silicone oils may also be used as inert organic liquid phase.

More particularly, the silicone oils that are suitable are liquid, non-volatile silicone fluids with a viscosity of less than or equal to 10 000 mPa·s at 25° C., the viscosity of the silicones being measured according to ASTM standard 445 Appendix C.

Silicone oils are defined in greater detail in Walter Noll's "Chemistry and Technology of Silicones" (1968)—Academic Press.

Among the silicone oils that may be used according to the invention, mention may be made especially of the silicone oils sold under the names DC-200 Fluid—5 mPa·s, DC-200 Fluid—20 mPa·s, DC-200 Fluid—350 mPa·s, DC-200 Fluid—1000 mPa·s and DC-200 Fluid—10 000 mPa·s by the company Dow Corning.

Mineral oils may also be used as inert organic liquid phase, for instance liquid paraffin.

Plant oils may also be suitable for use, and especially avocado oil, olive oil or liquid jojoba wax.

Preferably, the inert organic liquid phase is preferably from the polydecenes of formula $C_{10n}H_{[(20n)+2]}$ in which n ranges from 3 to 9 and preferably from 3 to 7, and esters of fatty alcohols or of fatty acids, and mixtures thereof.

According to one particular embodiment of the invention, the content of inert organic liquid phase in the anhydrous composition (A) ranges from 5% to 60% by weight, preferably from 10% to 50% by weight and even more preferentially from 15% to 45% by weight relative to the weight of the composition.

When composition (A) that is useful in the context of the invention is anhydrous, it may be in the form of a powder or a paste. Advantageously, the composition of the invention is in the form of a paste.

The aqueous composition(s) that are useful in the context of the invention may moreover comprise at least one organic solvent other than water to dissolve the reducing agents and/or the adjuvants that are not sufficiently water-soluble. Examples of organic solvents that may be mentioned include $C_1$-$C_4$ lower alkanols, such as ethanol and isopropanol; glycerol; glycols and glycol ethers, for instance 2-butoxyethanol, propylene glycol, dipropylene glycol, hexylene glycol, propylene glycol monomethyl ether, diethylene glycol monomethyl ether and monoethyl ether, and also aromatic alcohols, for instance benzyl alcohol or phenoxyethanol, similar products and mixtures thereof.

The solvents may then be present in proportions preferably of between 0.5% and 20% and more particularly between 2% and 10% by weight relative to the total weight of the stripping composition.

The aqueous composition (B) that is useful in the context of the invention comprises at least one organic acid with a pKa of less than or equal to 4, in the case where composition (A) is aqueous. The aqueous composition (B) may similarly comprise at least one such acid when composition (A) is anhydrous.

According to one particular embodiment of the invention, the organic acid(s) with a pKa of less than or equal to 4 are chosen from carboxylic acids, sulfonic acids and phosphonic acids. The acids of the invention may comprise in their structure one or more acid functions of identical or different nature (for example a carboxylic acid function and a sulfonic acid function).

These organic acids may be saturated or unsaturated, and, when they are unsaturated, they may contain in their structure one or more unsaturations.

They may be cyclic or acyclic, and, when they are cyclic, they may contain in their structure one or more rings, these rings being saturated or unsaturated, of heterocyclic nature with one or more heteroatoms chosen from O, N, S and P, or non-heterocyclic.

Preferably, the organic acids are chosen from carboxylic acids.

As examples of organic acids with a pKa of less than or equal to 4, mention may be made of the following acids: β-ketoglutaric acid, aceturic acid, angelic acid, atrolactic acid, benzenesulfonic acid, benzilic acid, benzoic acid, n-butylmalonic acid, β-chloropropionic acid, cinnamic acid, citric acid, fluoroacetic acid, fumaric acid, 2-furoic acid, gentisic acid, gluconic acid, glutaric acid, glyceric acid, glycolic acid, D-gulonic acid, hydroxyglutamic acid, lactic acid, mandelic acid, mefenamic acid, metanilic acid, o-orsellinic acid, phenoxyacetic acid, phenylacetic acid, pyrazinoic acid, pyruvic acid, salicylic acid, succinic acid, tartaric acid, tartronic acid, taurine, tricarballylic acid and trichloroacetic acid.

Preferably, the organic acid(s) with a pKa of less than or equal to 4 are chosen from α-hydroxy acids with a pKa of less than or equal to 4.

Even more preferentially, the organic acid(s) with a pKa of less than or equal to 4 are chosen from tartaric acid, lactic acid, citric acid and glycolic acid. Tartaric acid is most particularly preferred.

The organic acid(s) with a pKa of less than or equal to 4 are present in the aqueous composition (B) that is useful in the context of the invention in an amount preferably ranging between 1% and 40% by weight and preferably from 10% to 25% by weight relative to the total weight of the composition.

According to one particular embodiment of the invention, the (sulfinic acid derivatives of formula (I) and/or salts thereof)/(organic acids with a pKa of less than or equal to 4) weight ratio in the mixture of compositions (A) and (B) preferably ranges from 0.1 to 5 and even more preferentially from 0.2 to 1.5.

The pH of the aqueous composition (B) that is useful in the context of the invention is less than 5, preferably less than 4 and even more preferentially less than 3. It is adjusted using acidifying or basifying agents, in amounts ranging from 0.01% to 30% by weight relative to the total weight of the composition.

Among the acidifying agents, examples that may be mentioned include mineral or organic acids, for instance etidronic acid, hydrochloric acid, orthophosphoric acid, sulfuric acid, carboxylic acids, for instance acetic acid, tartaric acid, citric acid or lactic acid, and sulfonic acids. Mention may also be made of organic acids with a pKa of less than or equal to 4, as described previously.

Among the basifying agents, examples that may be mentioned include aqueous ammonia, alkali metal carbonates, alkanolamines, such as mono-, di- and triethanolamines and 2-methyl-2-amino-1-propanol and derivatives thereof, sodium hydroxide, potassium hydroxide and the compounds of formula (III) below:

in which W is a propylene residue optionally substituted with a hydroxyl group or a $C_1$-$C_4$ alkyl radical; and $R_7$, $R_8$, $R_9$ and $R_{10}$, which may be identical or different, represent a hydrogen atom or a $C_1$-$C_4$ alkyl or $C_1$-$C_4$ hydroxyalkyl radical.

According to one particular embodiment of the invention, the aqueous composition (B) comprises at least one fatty alcohol.

The fatty alcohol(s) may be chosen from non-(poly) oxyalkylenated alcohols (the alkyl containing 1 to 3 carbon atoms) and non-(poly)glycerolated alcohols, comprising one or more fatty chains containing from 10 to 30 carbon atoms, more particularly from 14 to 22 carbon atoms and even more advantageously from 16 to 18 carbon atoms, which are saturated or unsaturated, the fatty chains being optionally substituted with one or two additional hydroxyl groups. When the alcohol is unsaturated, it comprises from 1 to 3 conjugated or unconjugated carbon-carbon double bonds (—C=C—). Preferably, the fatty alcohol is a monoalcohol.

Examples of fatty alcohols that may be mentioned include lauryl alcohol, cetyl alcohol, stearyl alcohol, behenyl alcohol, myristyl alcohol, linoleyl alcohol, undecylenyl alcohol, palmitoleyl alcohol, linolenyl alcohol, arachidonyl alcohol, erucyl alcohol, isocetyl alcohol, isostearyl alcohol, isobehenyl alcohol and oleyl alcohol, and mixtures thereof.

Preferably, the aqueous composition (B) that is useful in the context of the invention comprises one or more saturated non-(poly)oxyalkylenated and non-(poly)glycerolated fatty monoalcohols, comprising from 14 to 22 carbon atoms and more precisely from 16 to 18 carbon atoms.

When the aqueous composition (B) that is useful in the context of the invention comprises at least one fatty alcohol, the said alcohol(s) are present in a content of between 0.1% and 20% by weight, preferably between 0.2% and 10% by weight, and, in accordance with an even more preferred variant of the invention, between 0.2% and 5% by weight relative to the total weight of composition (B).

The aqueous composition(s) that are useful in the context of the invention may be in various forms, such as in the form of solutions, emulsions, creams or gels.

Compositions (A) and (B) that are useful in the context of the invention may also contain various adjuvants conventionally used in stripping compositions, such as anionic, cationic, nonionic, amphoteric or zwitterionic surfactants or mixtures thereof, mineral or organic thickeners, and in particular anionic, cationic, nonionic and amphoteric polymeric associative thickeners, nonionic, anionic, amphoteric, zwitterionic or cationic conditioning polymers or mixtures thereof, preferably cationic or amphoteric substantive polymers, penetrants, sequestrants, fragrances, dispersants, volatile or non-volatile, modified or unmodified silicones, film-forming agents, ceramides, preserving agents, opacifiers, waxes and vitamins.

Needless to say, a person skilled in the art will take care to select this or these optional additional compound(s) such that the advantageous properties intrinsically associated with the stripping composition derived from the mixture of compositions (A) and (B) are not, or are not substantially, adversely affected by the envisaged addition(s).

According to one particular embodiment of the invention, the mixing ratio between the anhydrous or aqueous composition (A) and the aqueous composition (B) ranges from 0.1 to 10, preferentially from 0.2 to 4 and better still from 0.2 to 1.

The mixing ratio between the anhydrous or aqueous composition (A) and the aqueous composition (B) and the pH of the aqueous composition (B) are adjusted such that the pH of the mixture between compositions (A) and (B) is less than or equal to 5, preferably ranging from 2 to 5, more advantageously from 2 to 4 and even more preferentially from 2 to 3.

The temperature of application of the stripping composition derived from the mixture between compositions (A) and (B) is generally between 20 and 250° C. and preferably between 20 and 80° C.

The leave-on time sufficient for stripping the artificial colour from keratin fibres is generally between 1 minute and 120 minutes and preferably between 5 minutes and 60 minutes.

The application conditions, such as the application temperature and the leave-on time, the pH of the stripping composition and the amount of sulfinic acid derivatives of formula (I) as defined above, depend on the amount and nature of the artificial dyes to be removed, and also on the desired degree of bleaching.

As indicated previously, another subject of the invention is a composition comprising at least one sulfinic acid derivative of formula (I) and cosmetically acceptable salts thereof; and at least one thickener chosen from anionic polymers and nonionic polymers.

The sulfinic acid(s) and/or salts thereof may be present in the stripping composition according to the invention may be in proportions ranging from 0.01% to 20% and preferably from 0.1% to 10% by weight relative to the total weight of the composition.

According to the invention, the sulfinic acid(s) derivatives(s) are of formula (I). Everything that has been stated previously regarding the sulfinic derivatives of formula (I) and the salts thereof will not be repeated in this section of the description, and reference may be made thereto.

Moreover, the composition of the invention comprises at least one thickener chosen from anionic polymers and nonionic polymers.

For the purposes of the present invention, the term "thickening polymer" means a polymer which, when introduced at 1% by weight in an aqueous solution or an aqueous-alcoholic solution containing 30% ethanol, and at pH 7, or in an oil chosen from liquid petroleum jelly, isopropyl myristate or cyclopentadimethylsiloxane, makes it possible to achieve a viscosity of at least 100 cps and preferably of at least 500 cps, at 25° C. and at a shear rate of $1\ s^{-1}$. This viscosity may be measured using a cone/plate viscometer (Haake R600 rheometer or the like).

The thickening polymers that are useful in the context of the invention may be associative or non-associative anionic or nonionic polymers.

As regards the non-associative thickening polymers, it is first recalled that, for the purposes of the present invention, non-associative thickening polymers are thickening polymers not containing any $C_{10}$-$C_{30}$ fatty chains.

The thickening polymers may thicken the aqueous phase and/or the fatty phase.

Aqueous-phase-thickening polymers that may be mentioned include thickening polymers bearing sugar units.

For the purposes of the present invention, the term "sugar unit" means a unit derived from a carbohydrate of formula $C_n(H_2O)_{n-1}$ or $(CH_2O)_n$, which may be optionally modified by substitution and/or by oxidation and/or by dehydration.

The sugar units that may be included in the composition of the thickening polymers that are useful in the context of the invention are preferably derived from the following sugars: glucose, galactose, arabinose, rhamnose, mannose, xylose, fucose, anhydrogalactose, galacturonic acid, glucuronic acid, mannuronic acid, galactose sulfate, anhydrogalactose sulfate.

As thickening polymers that are useful in the context of the invention, mention may be made especially of:
native gums such as:
a) tree or shrub exudates, including:
gum arabic (branched polymer of galactose, arabinose, rhamnose and glucuronic acid);
ghatti gum (polymer derived from arabinose, galactose, mannose, xylose and glucuronic acid);
karaya gum (polymer derived from galacturonic acid, galactose, rhamnose and glucuronic acid);
gum tragacanth (or tragacanth) (polymer of galacturonic acid, galactose, fucose, xylose and arabinose);

b) gums derived from algae, including:
agar (polymer derived from galactose and anhydrogalactose);
alginates (polymers of mannuronic acid and of glucuronic acid);
carrageenans and furcellerans (polymers of galactose sulfate and of anhydrogalactose sulfate);
c) gums derived from seeds or tubers, including:
guar gum (polymer of mannose and galactose);
locust bean gum (polymer of mannose and galactose);
fenugreek gum (polymer of mannose and galactose);
tamarind gum (polymer of galactose, xylose and glucose);
konjac gum (polymer of glucose and mannose);
d) microbial gums, including:
xanthan gum (polymer of glucose, mannose acetate, mannose/pyruvic acid and glucuronic acid);
gellan gum (polymer of partially acylated glucose, rhamnose and glucuronic acid);
scleroglucan gum (glucose polymer);
e) plant extracts, including:
cellulose (glucose polymer);
starch (glucose polymer).

These polymers may be physically or chemically modified. A physical treatment that may especially be mentioned is the temperature.

Chemical treatments that may be mentioned include esterification, etherification, amidation or oxidation reactions. These treatments can lead to polymers that may be nonionic or anionic.

Preferably, these chemical or physical treatments are applied to guar gums, locust bean gums, starches and celluloses.

The nonionic guar gums that may be used according to the invention may be modified with $C_1$-$C_6$ hydroxyalkyl groups.

Among the hydroxyalkyl groups that may be mentioned, for example, are hydroxymethyl, hydroxyethyl, hydroxypropyl and hydroxybutyl groups.

These guar gums are well known in the prior art and can be prepared, for example, by reacting the corresponding alkene oxides such as, for example, propylene oxides, with the guar gum so as to obtain a guar gum modified with hydroxypropyl groups.

The degree of hydroxyalkylation preferably ranges from 0.4 to 1.2, and corresponds to the number of alkylene oxide molecules consumed by the number of free hydroxyl functions present on the guar gum.

Such nonionic guar gums optionally modified with hydroxyalkyl groups are sold, for example, under the trade names Jaguar HP8, Jaguar HP60 and Jaguar HP120 by the company Rhodia Chimie.

The botanical origin of the starch molecules used in the present invention may be cereals or tubers. Thus, the starches are chosen, for example, from corn starch, rice starch, cassava starch, barley starch, potato starch, wheat starch, sorghum starch and pea starch.

The starches may be chemically or physically modified especially by one or more of the following reactions: pregelatinization, oxidation, crosslinking, esterification, etherification, amidation, heat treatments.

More particularly, these reactions may be performed in the following manner:
pregelatinization by splitting the starch granules (for example drying and cooking in a drying drum);
oxidation with strong oxidizing agents, leading to the introduction of carboxyl groups into the starch molecule and to depolymerization of the starch molecule (for example by treating an aqueous starch solution with sodium hypochlorite);
crosslinking with functional agents capable of reacting with the hydroxyl groups of the starch molecules, which will thus bond together (for example with glyceryl and/or phosphate groups);
esterification in alkaline medium for the grafting of functional groups, especially $C_1$-$C_6$ acyl (acetyl), $C_1$-$C_6$ hydroxyalkyl (hydroxyethyl or hydroxypropyl), carboxymethyl or octenylsuccinic.

Monostarch phosphates (of the type Am—O—PO—$(OX)_2$), distarch phosphates (of the type Am—O—PO—(OX)—O—Am) or even tristarch phosphates (of the type Am—O—PO—(O—Am)$_2$) or mixtures thereof (Am meaning starch) may especially be obtained by crosslinking with phosphorus compounds.

X especially denotes alkali metals (for example sodium or potassium), alkaline-earth metals (for example calcium or magnesium), ammonium salts, amine salts, for instance those of monoethanolamine, diethanolamine, triethanolamine, 3-amino-1,2-propanediol, or ammonium salts derived from basic amino acids such as lysine, arginine, sarcosine, ornithine or citrulline.

The phosphorus compounds may be, for example, sodium tripolyphosphate, sodium orthophosphate, phosphorus oxychloride or sodium trimetaphosphate.

Distarch phosphates or compounds rich in distarch phosphate will preferentially be used, for instance the products sold under the references Prejel VA-70-T AGGL (gelatinized hydroxypropyl cassava distarch phosphate), Prejel TK1 (gelatinized cassava distarch phosphate) and Prejel 200 (gelatinized acetyl cassava distarch phosphate) by the company Avebe, or Structure Zea from National Starch (gelatinized corn distarch phosphate).

A preferred starch is a starch that has undergone at least one chemical modification such as at least one esterification.

As mentioned previously, the cellulose derivatives may be anionic or nonionic.

Among these derivatives, cellulose ethers, cellulose esters and cellulose ester ethers are distinguished.

Among the cellulose esters are inorganic esters of cellulose (cellulose nitrates, sulfates, phosphates, etc.), organic cellulose esters (cellulose monoacetates, triacetates, amidopropionates, acetatebutyrates, acetatepropionates and acetatetrimellitates, etc.), and mixed organic/inorganic esters of cellulose, such as cellulose acetatebutyrate sulfates and cellulose acetatepropionate sulfates. Among the cellulose ester ethers, mention may be made of hydroxypropylmethylcellulose phthalates and ethylcellulose sulfates.

Among the nonionic cellulose ethers that may be mentioned are alkylcelluloses such as methylcelluloses and ethylcelluloses (for example Ethocel Standard 100 Premium from Dow Chemical); hydroxyalkylcelluloses such as hydroxymethylcelluloses and hydroxyethylcelluloses (for example Natrosol 250 HHR sold by Aqualon) and hydroxypropylcelluloses (for example Klucel EF from Aqualon); mixed hydroxyalkyl-alkylcelluloses such as hydroxypropylmethylcelluloses (for example Methocel E4M from Dow Chemical), hydroxyethylmethylcelluloses, hydroxyethylethylcelluloses (for example Bermocoll E 481 FQ from Akzo Nobel) and hydroxybutylmethylcelluloses.

Among the anionic cellulose ethers, mention may be made of carboxyalkylcelluloses and salts thereof. Examples that may be mentioned include carboxymethylcelluloses, carboxymethylmethylcelluloses (for example Blanose 7M from the company Aqualon) and carboxymethylhydroxyethylcelluloses, and the sodium salts thereof.

Among the nonassociative thickening polymers not bearing sugar units that may be used, mention may be made of crosslinked acrylic or methacrylic acid homopolymers or copolymers, crosslinked 2-acrylamido-2-methylpropanesulfonic acid homopolymers and crosslinked acrylamide copolymers thereof, ammonium acrylate homopolymers, or copolymers of ammonium acrylate and of acrylamide, alone or mixtures thereof.

A first family of nonassociative thickening polymers that is suitable for use is represented by crosslinked acrylic acid homopolymers.

Among the homopolymers of this type, mention may be made of those crosslinked with an allyl alcohol ether of the sugar series, such as, for example, the products sold under the names Carbopol 980, 981, 954, 2984 and 5984 by the company Noveon or the products sold under the names Synthalen M and Synthalen K by the company 3 VSA.

The nonassociative thickening polymers may also be crosslinked (meth)acrylic acid copolymers, such as the polymer sold under the name Aqua SF1 by the company Noveon.

The nonassociative thickening polymers may be chosen from crosslinked 2-acrylamido-2-methylpropanesulfonic acid homopolymers and the crosslinked acrylamide copolymers thereof.

As regards these homopolymers and copolymers, which may be partially or totally neutralized, mention may be made of polymers comprising from 90% to 99.9% by weight, relative to the total weight of the polymer, of units of formula (j) below:

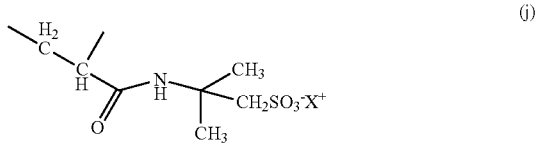

in which $X^+$ denotes a cation or a mixture of cations, or a proton.

More particularly, the cations are chosen from alkali metals (for instance sodium or potassium), ammonium ions optionally substituted with 1 to 3 alkyl radicals, which may be identical or different, containing from 1 to 6 carbon atoms, optionally bearing at least one hydroxyl radical, cations derived from N-methylglucamine or from basic amino acids, for instance arginine and lysine. Preferably, the cation is an ammonium or sodium ion.

Moreover, the polymer comprises from 0.01% to 10% by weight, relative to the total weight of the polymer, of crosslinking units derived from at least one monomer containing at least two ethylenic unsaturations (carbon-carbon double bond).

The crosslinking monomers containing at least two ethylenic unsaturations are chosen, for example, from diallyl ether, triallyl cyanurate, diallyl maleate, allyl (meth)acrylate, dipropylene glycol diallyl ether, polyglycol diallyl ethers, triethylene glycol divinyl ether, hydroquinone diallyl ether, tetraallyloxyethane, tetra- or diethylene glycol di(meth)acrylate, triallylamine, tetraallylethylenediamine, trimethylolpropane diallyl ether, trimethylolpropane triacrylate, methylenebis(meth)acrylamide or divinylbenzene, allylic ethers of alcohols of the sugar series, or other allylic or vinyl ethers of polyfunctional alcohols, and also allylic esters of phosphoric and/or vinylphosphonic acid derivatives, or mixtures of these compounds.

For further details regarding these polymers, reference may be made to document EP 815 828.

Among the partially or totally neutralized crosslinked copolymers of 2-acrylamido-2-methylpropanesulfonic acid and of acrylamide, mention may be made in particular of the product described in Example 1 of document EP 503 853, and reference may be made to said document as regards these polymers.

The composition may similarly comprise, as nonassociative thickening polymers, ammonium acrylate homopolymers or copolymers of ammonium acrylate and of acrylamide.

Among the ammonium acrylate homopolymers that may be mentioned is the product sold under the name Microsap PAS 5193 by the company Hoechst. Among the copolymers of ammonium acrylate and of acrylamide that may be mentioned is the product sold under the name Bozepol C Nouveau or the product PAS 5193 sold by the company Hoechst. Reference may be made especially to documents FR 2 416 723, U.S. Pat. Nos. 2,798,053 and 2,923,692 as regards the description and preparation of such compounds.

Among the thickeners, mention may also be made of thickening systems based on associative polymers of nonionic or anionic nature that are well known to those skilled in the art.

It is recalled that associative polymers are polymers that are capable, in an aqueous medium, of reversibly associating with each other or with other molecules.

Their chemical structure more particularly comprises at least one hydrophilic region and at least one hydrophobic region.

The term "hydrophobic group" means a radical or polymer with a saturated or unsaturated, linear or branched hydrocarbon-based chain, comprising at least 10 carbon atoms, preferably from 10 to 30 carbon atoms, in particular from 12 to 30 carbon atoms and more preferentially from 18 to 30 carbon atoms.

Preferentially, the hydrocarbon-based group is derived from a monofunctional compound. By way of example, the hydrophobic group may be derived from a fatty alcohol such as stearyl alcohol, dodecyl alcohol or decyl alcohol. It may also denote a hydrocarbon-based polymer, for instance polybutadiene.

Among the associative polymers of anionic type that may be mentioned are:

(I) those comprising at least one hydrophilic unit and at least one fatty-chain allyl ether unit, more particularly those whose hydrophilic unit is formed by an ethylenic unsaturated anionic monomer, more particularly a vinylcarboxylic acid and most particularly an acrylic acid or a methacrylic acid or mixtures thereof, the fatty-chain allyl ether unit of which corresponds to the monomer of formula (III) below:

in which R' denotes H or $CH_3$, B denotes an ethylenoxy radical, n is zero or denotes an integer ranging from 1 to 100, R denotes a hydrocarbon-based radical chosen from alkyl, arylalkyl, aryl, alkylaryl and cycloalkyl radicals, containing from 8 to 30 carbon atoms, preferably 10 to 24 carbon atoms and even more particularly from 12 to 18 carbon atoms. A unit of formula (III) that is more particularly preferred is a unit in which R' denotes H, n is equal to 10 and R denotes a stearyl ($C_{18}$) radical.

Anionic associative polymers of this type are described and prepared, according to an emulsion polymerization process, in patent EP-0 216 479.

Among these anionic associative polymers, those that are particularly preferred according to the invention are polymers formed from 20% to 60% by weight of acrylic acid and/or of methacrylic acid, from 5% to 60% by weight of lower alkyl (meth)acrylates, from 2% to 50% by weight of fatty-chain allyl ether of formula (III), and from 0 to 1% by weight of a crosslinking agent which is a well-known copolymerizable unsaturated polyethylenic monomer, for instance diallyl phthalate, allyl (meth)acrylate, divinylbenzene, (poly)ethylene glycol dimethacrylate or methylenebisacrylamide.

Among the latter polymers, those most particularly preferred are crosslinked terpolymers of methacrylic acid, of ethyl acrylate and of polyethylene glycol (10 EO) stearyl alcohol ether (Steareth-10), in particular those sold by the company Ciba under the names Salcare SC 80® and Salcare SC 90®, which are aqueous 30% emulsions of a crosslinked terpolymer of methacrylic acid, of ethyl acrylate and of steareth-10 allyl ether (40/50/10);

(II) those comprising at least one hydrophilic unit of unsaturated olefinic carboxylic acid type, and at least one hydrophobic unit of ($C_{10}$-$C_{30}$)alkyl ester of unsaturated carboxylic acid type.

These polymers are preferably chosen from those in which the hydrophilic unit of unsaturated olefinic carboxylic acid type corresponds to the monomer of formula (IV) below:

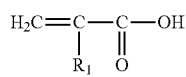

(IV)

in which R1 denotes H, $CH_3$, or $C_2H_5$, i.e. acrylic acid, methacrylic acid or ethacrylic acid units, and in which the hydrophobic unit of ($C_{10}$-$C_{30}$)alkyl ester of unsaturated carboxylic acid type corresponds to the monomer of formula (V) below:

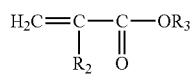

(V)

in which R2 denotes H or $CH_3$ or $C_2H_5$ (i.e. acrylate, methacrylate or ethacrylate units) and preferably H (acrylate units) or $CH_3$ (methacrylate units), R3 denoting a $C_{10}$-$C_{30}$ and preferably $C_{12}$-$C_{22}$ alkyl radical.

(C10-C30) alkyl esters of unsaturated carboxylic acids according to the invention include, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to patents U.S. Pat. Nos. 3,915,921 and 4,509,949.

Among the anionic associative polymers of this type that will be used more particularly are polymers formed from a monomer mixture comprising:

essentially acrylic acid,
an ester of formula (V) described above in which R2 denotes H or $CH_3$, R3 denoting an alkyl radical containing from 12 to 22 carbon atoms, and a crosslinking agent, which is a well-known copolymerizable unsaturated polyethylenic monomer, for instance diallyl phthalate, allyl(meth)acrylate, divinylbenzene, (poly)ethylene glycol dimethacrylate and methylenebisacrylamide.

Among anionic associative polymers of this type that will be used more particularly are those consisting of from 95% to 60% by weight of acrylic acid (hydrophilic unit), 4% to 40% by weight of $C_{10}$-$C_{30}$ alkyl acrylate (hydrophobic unit) and 0% to 6% by weight of crosslinking polymerizable monomer, or alternatively those consisting of from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described above.

Among said above polymers, those most particularly preferred according to the present invention are the products sold by the company Goodrich under the trade names Pemulen TR1®, Pemulen TR2® and Carbopol 1382®, and even more preferentially Pemulen TR1®, and the product sold by the company SEPPIC under the name Coatex SX®.

Mention may also be made of polymers which, besides the monomers of formula (IV) and of formula (V), contain one or more other monomers. This additional monomer may especially be a vinyllactam and in particular vinylpyrrolidone.

An example of a polymer that may be mentioned is the acrylic acid/lauryl methacrylate/vinylpyrrolidone terpolymer sold under the name Acrylidone LM by the company ISP;

(III) maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name Performa V 1608® by the company Newphase Technologies.

(IV) acrylic terpolymers comprising:
(a) about 20% to 70% by weight of a carboxylic acid containing α,β-monoethylenic unsaturation,
(b) about 20% to 80% by weight of a non-surfactant monomer containing α,β-monoethylenic unsaturation other than (a),
(c) about 0.5% to 60% by weight of a nonionic monourethane which is the product of reaction of a monohydric surfactant with a monoisocyanate containing monoethylenic unsaturation, such as those described in patent application EP-A-0 173 109 and more particularly the terpolymer described in Example 3, namely a methacrylic acid/methyl acrylate/behenyl alcohol dimethyl-meta-isopropenylbenzylisocyanate ethoxylated (40 EO) terpolymer, as an aqueous 25% dispersion.

(V) copolymers comprising among their monomers an α,β-monoethylenically unsaturated carboxylic acid and an ester of an α,β-monoethylenically unsaturated carboxylic acid and of an oxyalkylenated fatty alcohol.

Preferentially, these compounds also comprise as monomer an ester of an α,β-monoethylenically unsaturated carboxylic acid and of a $C_1$-$C_4$ alcohol.

An example of a compound of this type that may be mentioned is Aculyn 22® sold by the company Röhm & Haas, which is a methacrylic acid/ethyl acrylate/oxyalkylenated stearyl methacrylate terpolymer.

(VI) amphiphilic polymers comprising at least one ethylenically unsaturated monomer bearing a sulfonic group, in free or partially or totally neutralized form and comprising at least one hydrophobic part. These polymers may be crosslinked or noncrosslinked. They are preferably crosslinked.

The ethylenically unsaturated monomers bearing a sulfonic group are especially chosen from vinylsulfonic acid, styrenesulfonic acid, (meth)acrylamido($C_1$-$C_{22}$)alkylsulfonic acids, N—($C_1$-$C_{22}$)alkyl(meth)acrylamido($C_1$-$C_{22}$)alkylsulfonic acids such as undecylacrylamidomethanesulfonic acid, and also partially or totally neutralized forms thereof, and mixtures thereof.

(Meth)acrylamido($C_1$-$C_{22}$)alkylsulfonic acids, for instance acrylamidomethanesulfonic acid, acrylamidoethanesulfonic acid, acrylamidopropanesulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid or 2-acrylamido-2,6-dimethyl-3-heptanesulfonic acid, and also partially or totally neutralized forms thereof, will more preferentially be used.

2-Acrylamido-2-methylpropanesulfonic acid (AMPS), and also partially or totally neutralized forms thereof, will more particularly be used.

The polymers of this family may be chosen especially from random amphiphilic AMPS polymers modified by reaction with a $C_6$-$C_{22}$ n-monoalkylamine or di-n-alkylamine, and such as those described in patent application WO 00/31154, which form an integral part of the content of the description. These polymers may also contain other ethylenically unsaturated hydrophilic monomers selected, for example, from (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

The preferred polymers of this family are chosen from amphiphilic copolymers of AMPS and of at least one ethylenically unsaturated hydrophobic monomer.

These same copolymers may also contain one or more ethylenically unsaturated monomers not comprising a fatty chain, such as (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

These copolymers are described especially in patent application EP-A-750 899, patent U.S. Pat. No. 5,089,578 and in the following publications from Yotaro Morishima:

Self-assembling amphiphilic polyelectrolytes and their nanostructures, Chinese Journal of Polymer Science, Vol. 18, No. 40, (2000), 323-336;

Micelle formation of random copolymers of sodium 2-(acrylamido)-2-methylpropanesulfonate and a nonionic surfactant macromonomer in water as studied by fluorescence and dynamic light scattering, Macromolecules, 2000, Vol. 33, No. 10-3694-3704;

Solution properties of micelle networks formed by nonionic moieties covalently bound to a polyelectrolyte: salt effects on rheological behavior—Langmuir, 2000, Vol. 16, No. 12, 5324-5332;

Stimuli responsive amphiphilic copolymers of sodium 2-(acrylamido)-2-methylpropanesulfonate and associative macromonomers, Polym. Preprint, Div. Polym. Chem. 1999, 40(2), 220-221.

The ethylenically unsaturated hydrophobic monomers of these particular copolymers are preferably selected from the acrylates or acrylamides of formula (VI) below:

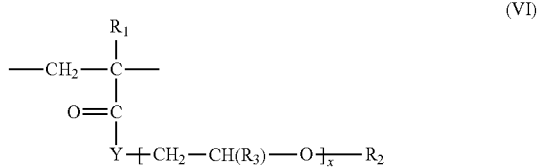

in which R1 and R3, which may be identical or different, denote a hydrogen atom or a linear or branched $C_1$-$C_6$ alkyl radical (preferably methyl); Y denotes O or NH; R2 denotes a hydrophobic hydrocarbon-based radical containing at least 8 and more preferentially from 8 to 22 carbon atoms, even more preferentially from 8 to 18 carbon atoms and more particularly from 12 to 18 carbon atoms; x denotes a number of moles of alkylene oxide and ranges from 0 to 100.

The radical R2 is preferably selected from linear $C_8$-$C_{18}$ alkyl radicals (for example n-hexyl, n-octyl, n-decyl, n-hexadecyl or n-dodecyl radicals); branched $C_8$-$C_{18}$ alkyl radicals; cyclic $C_8$-$C_{18}$ alkyl radicals (for example cyclododecane ($C_{12}$) or adamantane ($C_{10}$) radicals); $C_6$-$C_{18}$ alkylperfluoro radicals (for example the group of formula —$(CH_2)_9$—$(CF_2)_9$—$CF_3$); the cholesteryl ($C_{27}$) radical or a cholesterol ester residue, such as the cholesteryl oxyhexanoate group; or polycyclic aromatic groups, such as naphthalene or pyrene. Among these radicals, the ones that are more particularly preferred are linear alkyl radicals and more particularly the n-dodecyl radical.

According to one particularly preferred form of the invention, the monomer of formula (VI) comprises at least one alkylene oxide unit (x≥1) and preferably a polyoxyalkylenated chain. The polyoxyalkylenated chain is preferably constituted of ethylene oxide units and/or of propylene oxide units and more particularly still constituted of ethylene oxide units. The number of oxyalkylene units generally ranges from 3 to 100, more preferably from 3 to 50 and more preferably still from 5 to 30.

Among these polymers, mention may be made of:

crosslinked or noncrosslinked, neutralized or non-neutralized copolymers comprising from 15% to 60% by weight of AMPS units and from 40% to 85% by weight of ($C_8$-$C_{16}$)alkyl (meth)acrylamide units or of ($C_8$-$C_{16}$) alkyl (meth)acrylate units relative to the polymer, such as those described in patent application EP-A 750 899;

terpolymers comprising from 10 mol % to 90 mol % of acrylamide units, from 0.1 mol % to 10 mol % of AMPS units and from 5 mol % to 80 mol % of n-($C_6$-$C_{18}$)alkylacrylamide units, such as those described in U.S. Pat. No. 5,089,578.

Mention may also be made of copolymers of totally neutralized AMPS and of dodecyl methacrylate, and also crosslinked and non-crosslinked copolymers of AMPS and of n-dodecylmethacrylamide, such as those described in the Morishima articles mentioned above.

Mention will be made more particularly of the copolymers constituted of 2-acrylamido-2-methylpropanesulfonic acid (AMPS) units of formula (VII) below:

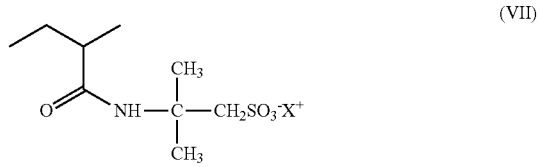

in which X⁺ is a proton, an alkali metal cation, an alkaline-earth metal cation or an ammonium ion;
and units of formula (VIII) below:

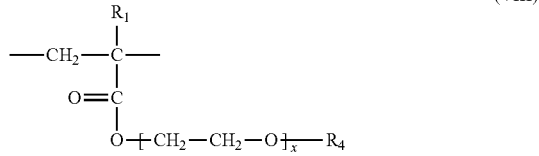

in which x denotes an integer varying from 3 to 100, preferably from 3 to 50, and more preferably from 5 to 30; $R_1$ has the same meaning as that indicated above in formula (I) and $R_4$ denotes a linear or branched $C_6$-$C_{22}$ and more preferably $C_{12}$-$C_{18}$ or $C_{10}$-$C_{22}$ alkyl.

The polymers that are particularly preferred are those for which x=25, $R_1$ denotes methyl and $R_4$ represents n-dodecyl; they are described in the Morishima articles mentioned above.

The molar percentage concentration of units of formula (VII) and of units of formula (VIII) will vary as a function of the desired cosmetic application and of the rheological properties sought for the formulation. It will preferably range from 70 mol % to 99 mol % of AMPS units and from 1 mol % to 30 mol % of units of formula (VIII) relative to the copolymer, and more particularly from 70 mol % to 90 mol % of AMPS units and from 10 mol % to 30 mol % of units of formula (VIII).

The polymers for which X⁺ denotes sodium or ammonium are more particularly preferred.

The associative polymers of nonionic type that are useful in the context of the invention are preferably chosen from:

(a) copolymers of vinylpyrrolidone and of fatty-chain hydrophobic monomers, of which examples that may be mentioned include:
   the products Antaron V216® and Ganex V216® (vinylpyrrolidone/hexadecene copolymer) sold by the company ISP,
   the products Antaron V220® and Ganex V220® (vinylpyrrolidone/eicosene copolymer) sold by the company ISP.

(b) copolymers of $C_1$-$C_6$ alkyl methacrylates or acrylates and of amphiphilic monomers comprising at least one fatty chain, such as, for example, the oxyethylenated methyl acrylate/stearyl acrylate copolymer sold by the company Goldschmidt under the name Antil 208®.

(c) copolymers of hydrophilic methacrylates or acrylates and of hydrophobic monomers comprising at least one fatty chain, for instance the polyethylene glycol methacrylate/lauryl methacrylate copolymer.

(d) polyurethane polyethers comprising in their chain both hydrophilic blocks usually of polyoxyethylenated nature and hydrophobic blocks, which may be aliphatic sequences alone and/or cycloaliphatic and/or aromatic sequences.

(e) polymers with an aminoplast ether backbone containing at least one fatty chain, such as the Pure Thix® compounds sold by the company Sud-Chemie.

(f) celluloses or derivatives thereof, modified with groups comprising at least one fatty chain, such as alkyl, arylalkyl or alkylaryl groups or mixtures thereof in which the alkyl groups are of $O_8$, and in particular:
   nonionic alkylhydroxyethylcelluloses such as the products Natrosol Plus Grade 330 CS and Polysurf 67 ($C_{16}$ alkyl) sold by the company Aqualon;
   nonionic nonoxynylhydroxyethylcelluloses such as the product Amercell HM-1500 sold by the company Amerchol;
   nonionic alkylcelluloses such as the product Bermocoll EHM 100 sold by the company Berol Nobel;

(g) associative guar derivatives, for instance hydroxypropyl guars modified with a fatty chain, such as the product Esaflor HM 22 (modified with a $C_{22}$ alkyl chain) sold by the company Lamberti; the product Miracare XC 95-3 (modified with a $C_{14}$ alkyl chain) and the product RE 205-146 (modified with a $C_{20}$ alkyl chain) sold by Rhodia Chimie.

Preferably, the polyurethane polyethers comprise at least two hydrocarbon-based lipophilic chains containing from 6 to 30 carbon atoms, separated by a hydrophilic block, the hydrocarbon-based chains possibly being pendent chains or chains at the end of the hydrophilic block. In particular, it is possible for one or more pendent chains to be included. In addition, the polymer may comprise a hydrocarbon-based chain at one end or at both ends of a hydrophilic block.

The polyurethane polyethers may be multiblock, in particular in triblock form. The hydrophobic blocks may be at each end of the chain (for example: triblock copolymer containing a hydrophilic central block) or distributed both at the ends and in the chain (for example multiblock copolymer). These same polymers may also be graft polymers or star polymers.

The nonionic fatty-chain polyurethane polyethers may be triblock copolymers in which the hydrophilic block is a polyoxyethylenated chain comprising from 50 to 1000 oxyethylene groups. The nonionic polyurethane polyethers comprise a urethane bond between the hydrophilic blocks, whence arises the name.

By extension, also included among the nonionic fatty-chain polyurethane polyethers are those in which the hydrophilic blocks are linked to the lipophilic blocks via other chemical bonds.

As examples of nonionic fatty-chain polyurethane polyethers that may be used in the invention, it is also possible to use Rheolate 205® containing a urea function, sold by the company Rheox, or Rheolate® 208, 204 or 212, and also Acrysol RM 184®.

Mention may also be made of the product Elfacos T210® containing a $C_{12}$-$C_{14}$ alkyl chain, and the product Elfacos T212® containing a $O_{18}$ alkyl chain, from Akzo.

The product DW 1206B® from Röhm & Haas containing a $C_{20}$ alkyl chain and a urethane bond, sold at a solids content of 20% in water, may also be used.

It is also possible to use solutions or dispersions of these polymers, especially in water or in aqueous-alcoholic medium. Examples of such polymers that may be mentioned are Rheolate® 255, Rheolate® 278 and Rheolate® 244 sold by the company Rheox. The products DW 1206F and DW 1206J sold by the company Röhm & Haas may also be used.

The polyurethane polyethers that may be used according to the invention are in particular those described in the article by G. Fonnum, J. Bakke and Fk. Hansen—Colloid Polym. Sci 271, 380.389 (1993).

It is even more particularly preferred to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold especially by the company Röhm & Haas under the names Aculyn 46® and Aculyn 44® [Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%)].

Even more preferentially, the aqueous-phase thickening polymer(s) of the invention are chosen from associative or non-associative polymers bearing sugar units, associative or non-associative acrylic or methacrylic anionic polymers, and associative or non-associative polyurethanes.

According to one particular embodiment of the invention, the polymers for structuring the oily phase via physical interactions are chosen from polyamides, silicone polyamides, saccharide or polysaccharide mono- or polyalkyl esters, N-acylamino acid amide derivatives, and copolymers comprising an alkylene or styrene block, these copolymers possibly being diblock, triblock, multiblock or radial-block polymers, also known as star copolymers, or alternatively comb polymers.

1) Polymers Bearing at Least One Crystallizable Block in the Backbone

These are also polymers that are soluble or dispersible in the oil or fatty phase by heating above their melting point m.p. These polymers are especially block copolymers consisting of at least two blocks of different chemical nature, one of which is crystallizable.

As polymers bearing in the backbone at least one crystallizable block that are suitable for use in the invention, mention may be made of:

i) the polymers defined in document U.S. Pat. No. 5,156,911;

ii) block copolymers of olefin or of cycloolefin containing a crystallizable chain, for instance those derived from the block polymerization of:

cyclobutene, cyclohexene, cyclooctene, norbornene (i.e. bicyclo(2,2,1)-2-heptene), 5-methylnorbornene, 5-ethylnorbornene, 5,6-dimethyl-norbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a,5,8a-octahydro-naphthalene, dicyclopentadiene, or mixtures thereof, with ethylene, propylene, 1-butene, 3-methyl-1-butene, 1-hexene, 4-methyl-1-pentene, 1-octene, 1-decene or 1-eicosene, or mixtures thereof. These block copolymers may be in particular (ethylene/norbornene) block copolymers and (ethylene/propylene/ethylidenenorbornene) block terpolymers.

Those resulting from the block copolymerization of at least two $C_2$-$C_{16}$, and better still $C_2$-$C_{12}$, α-olefins such as those mentioned above and in particular block bipolymers of ethylene and of 1-octene may also be used.

Copolymers containing at least one crystallizable block, the rest of the copolymer being amorphous (at room temperature). These copolymers may also contain two crystallizable blocks of different chemical nature. The preferred copolymers are those that simultaneously contain at room temperature a crystallizable block and an amorphous block that are both hydrophobic and lipophilic, sequentially distributed; mention may be made, for example, of polymers containing one of the crystallizable blocks and one of the amorphous blocks below:

Block that is crystallizable by nature: a) of polyester type, for instance poly(alkylene terephthalate), b) of polyolefin type, for instance polyethylenes or polypropylenes.

Amorphous and lipophilic block, for instance: amorphous polyolefins or copoly(olefin)s such as poly(isobutylene), hydrogenated polybutadiene or hydrogenated poly(isoprene).

As examples of such copolymers containing a crystallizable block and an amorphous block, mention may be made of:

a) poly(δ-caprolactone)-b-poly(butadiene) block copolymers, preferably used hydrogenated, such as those described in the article "Melting behaviour of poly(δ-caprolactone)-block-polybutadiene copolymers" from S, Nojima, Macromolecules, 32, 3727-3734 (1999), b) the hydrogenated block or multiblock poly(butylene terephthalate)-b-poly(isoprene) block copolymers cited in the article "Study of morphological and mechanical properties of PP/PBT" by B. Boutevin et al., Polymer Bulletin, 34, 117-123 (1995), c) the poly(ethylene)-b-copoly(ethylene/propylene) block copolymers cited in the articles "Morphology of semicrystalline block copolymers of ethylene-(ethylene-alt-propylene)" by P. Rangarajan et al., Macromolecules, 26, 4640-4645 (1993) and "Polymer aggregates with crystalline cores: the system poly(ethylene)poly(ethylene-propylene)" P. Richter et al., Macromolecules, 30, 1053-1068 25 (1997).

d) the poly(ethylene)-b-poly(ethylethylene) block copolymers cited in the general article "Crystallization in block copolymers" by I. W. Hamley, Advances in Polymer Science, Vol. 148, 113-137 (1999).

The semi-crystalline polymers that may be used in the context of the invention may be non-crosslinked or partially crosslinked, provided that the degree of crosslinking does not impede their dissolution or dispersion in the liquid oily phase by heating above their melting point. It may then be a case of chemical crosslinking, by reaction with a multifunctional monomer during the polymerization. It may also be a case of physical crosslinking, which may then be due either to the establishment of bonds of hydrogen or dipolar type between groups borne by the polymer, for instance dipolar interactions between carboxylate ionomers, these interactions being in small amount and borne by the polymer backbone; or due to a phase separation between the crystallizable blocks and the amorphous blocks borne by the polymer.

Preferably, the semi-crystalline polymers that are suitable for the invention are non-crosslinked.

As particular examples of semi-crystalline polymers that may be used in the composition according to the invention, mention may be made of the Intelimer® products from the company Landec described in the brochure "Intelimer® polymers". These polymers are in solid form at room temperature (25° C.). They bear crystallizable side chains and contain the monomer as defined in formula X above. Mention may be made especially of "Landec IP22®", with a melting point m.p. of 56° C., which is a viscous, impermeable, non-tacky product at room temperature.

It is also possible to use the semi-crystalline polymers described in Examples 3, 4, 5, 7 and 9 of U.S. Pat. No. 5,156,911, resulting from the copolymerization of acrylic acid and of $C_5$ to $C_{16}$ alkyl (meth)acrylate, such as those resulting from the copolymerization:

of acrylic acid, of hexadecyl acrylate and of isodecyl acrylate in a 1/16/3 ratio, of acrylic acid and of pentadecyl acrylate in a 1/19 ratio, of acrylic acid, of hexadecyl acrylate and of ethyl acrylate in a 2.5/76.5/20 ratio, of acrylic acid, of hexadecyl acrylate and of methyl acrylate in a 5/85/10 ratio, of acrylic acid and of octadecyl (meth)acrylate in a 2.5/97.5 ratio.

It is also possible to use the polymer "Structure O" sold by the company National Starch, such as the product described in document U.S. Pat. No. 5,736,125, of m.p. 44° C., and also semi-crystalline polymers containing crystallizable side chains comprising fluoro groups as described in Examples 1, 4, 6, 7 and 8 of document WO-A-01/19333.

It is also possible to use the semi-crystalline polymers obtained by copolymerization of stearyl acrylate and of acrylic acid or of NVP, or by copolymerization of behenyl acrylate and of acrylic acid or NVP, as described in document U.S. Pat. No. 5,519,063 or EP-A-0 550 745.

According to one particular embodiment variant, the semi-crystalline polymers that are suitable for use in the present invention are especially alkyl acrylates, among which mention may be made of the Landec copolymers:

Doresco IPA 13-1®: polystearyl acrylate, m.p. of 49° C. and MW of 145 000;

Doresco IPA 13-3®: polyacrylate/methacrylic acid, m.p. of 65° C. and MW of 114 000;

Doresco IPA 13-4®: polyacrylate/vinylpyrrolidone, m.p. of 44° C. and MW of 387 000;

Doresco IPA13-5®: polyacrylate/hydroxyethyl methacrylate, m.p. of 47° C. and MW of 397 600;

Doresco IPA 13-6®: polybehenyl acrylate, m.p. of 66° C.

2) Non-Silicone Polyamides

The particular polyamides used in the composition according to the invention are preferably those described in document U.S. Pat. No. 5,783,657 from the company Union Camp. The section of U.S. Pat. No. 5,783,657 devoted to these polymers is incorporated by reference.

Each of these polyamides especially satisfies the following formula:

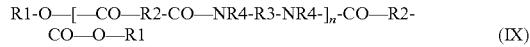

R1—O—[—CO—R2—CO—NR4-R3-NR4-]$_n$-CO—R2-CO—O—R1    (IX)

in which n denotes a number of amide units such that the number of ester groups represents from 10% to 50% of the total number of ester and amide groups; R1 is, independently in each case, an alkyl or alkenyl group containing at least 4 carbon atoms and in particular from 4 to 24 carbon atoms; R2 represents, independently in each case, a $C_4$ to $C_{55}$ hydrocarbon-based group, on condition that 50% of the groups R2 represent a $C_{30}$ to $C_{55}$ hydrocarbon-based group; R3 represents, independently in each case, an organic group containing at least 2 carbon atoms, hydrogen atoms and optionally one or more oxygen or nitrogen atoms; and R4 represents, independently in each case, a hydrogen atom, a $C_1$ to $C_{10}$ alkyl group or a direct bond to R3 or to another R4, such that the nitrogen atom to which R3 and R4 are both attached forms part of a heterocyclic structure defined by R4-N—R3, with at least 50% of the groups R4 representing a hydrogen atom. In particular, the ester groups of this polyamide represent from 15% to 40% and at best from 20% to 35% of the total number of ester and amide groups. Furthermore, n advantageously represents an integer ranging from 1 to 10 and better still from 1 to 5, limits inclusive.

Preferably, R1 is a $C_{12}$ to $C_{22}$ and preferably $C_{16}$ to $C_{22}$ alkyl group. Advantageously, R2 may be a $C_{10}$ to $C_{42}$ hydrocarbon-based (alkylene) group. Preferably, at least 50% and better still at least 75% of the groups R2 are groups containing from 30 to 42 carbon atoms. The other groups R2 are $C_4$ to $C_{19}$ and better still $C_4$ to $C_{12}$ hydrogen-containing groups. Preferably, R3 represents a $C_2$ to $C_{36}$ hydrocarbon-based group or a polyoxyalkylene group and R4 represents a hydrogen atom. Preferably, R3 represents a saturated or unsaturated $C_2$ to $C_{12}$ hydrocarbon-based group. The hydrocarbon-based groups may be linear, cyclic or branched, and saturated or unsaturated groups. Moreover, the alkyl and alkylene groups may be linear or branched, and saturated or unsaturated groups.

The thickening of the oily phase may be obtained by means of one or more polyamides defined above. In general, these polyamides are in the form of mixtures, these mixtures also possibly containing a synthetic product corresponding to a polyamide as defined above with n being 0, i.e. a diester.

As structuring polyamides that may be used in the invention, mention may also be made of polyamide resins resulting from the condensation of an aliphatic dicarboxylic acid and a diamine (including compounds containing, respectively, more than two carboxyl groups and more than two amine groups), the carboxyl and amine groups of adjacent individual units being condensed in the form of an amide bond. These polyamide resins are especially the products sold under the brand name Versamid® by the companies General Mills, Inc. and Henkel Corp., under the brand name Onamid®, especially Onamid S or C. These resins have a weight-average molecular mass ranging from 6000 to 9000. For further information regarding these polyamides, reference may be made to U.S. Pat. Nos. 3,645,705 and 3,148,125. Use is made more especially of Versamid® 30 or 744.

It is also possible to use the polyamides sold or manufactured by the company Arizona under the references Uni-Rez (2658, 2931, 2970, 2621, 2613, 2624, 2665, 1554, 2623, 2662) and the product sold under the reference Macromelt 6212 by the company Henkel. For further information regarding these polyamides, reference may be made to document U.S. Pat. No. 5,500,209.

As examples of structuring polyamides that may be used in the composition according to the invention, mention may also be made of the commercial products sold or manufactured by the company Arizona Chemical under the names Uniclear 80 and Uniclear 100. They are sold, respectively, in the form of an 80% (active material) gel and a 100% (active material) gel in a mineral oil. They have a softening point of from 88 to 105° C. These commercial products are a mixture of copolymers of a $C_{36}$ diacid coupled with ethylenediamine, having a weight-average molecular mass of about 6000. The terminal ester groups result from the esterification of the remaining acid end groups with cetyl alcohol, stearyl alcohol or mixtures thereof (also known as cetylstearyl alcohol).

3) Silicone Polyamides

The polymers (homopolymers or copolymers) of silicone polyamide type that are suitable for use in the invention have an average molecular mass included in the range from 500 to 500 000 and contain at least one group comprising:

at least one polyorganosiloxane group, comprising from 1 to 1000 organosiloxane units, in the chain of the group or in the form of a graft, and at least two groups capable of establishing hydrogen interactions, chosen from ester, amide, sulfonamide, carbamate, thiocarbamate, urea, thiourea, oxamido, guanidino and biguanidino groups, and combinations thereof, on condition that at least one of these groups is other than an ester group, the polymer being solid at room temperature and soluble in the oily phase at a temperature ranging from 25 to 120° C.

The polymers of silicone polyamide type that are suitable for use in the invention, and used as oil-structuring agent, may belong to the following two families:

polyorganosiloxanes comprising at least two groups capable of establishing hydrogen interactions, these two groups being located in the polymer chain, and/or polyorganosiloxanes comprising at least two groups capable of establishing hydrogen interactions, these two groups being located on grafts or branches.

The polymers of silicone polyamide type comprising two groups capable of establishing hydrogen interactions in the polymer chain may be polymers comprising at least one unit corresponding to the first formula below:

$$-\left[\left[\begin{array}{c}R^1\\|\\Si-O\\|\\R^3\end{array}\right]_m\begin{array}{c}R^2\\|\\Si-X-G-Y-G-X\\|\\R^4\end{array}\right]_n-$$

in which:

R1, R2, R3 and R4, which may be identical or different, represent a group chosen from:

saturated or unsaturated, $C_1$ to $C_{40}$ linear, branched or cyclic hydrocarbon-based groups, which may contain in their chain one or more oxygen, sulfur and/or nitrogen atoms, and which may be partially or totally substituted with fluorine atoms, $C_6$ to $C_{10}$ aryl groups, optionally substituted with one or more $C_1$ to $C_4$ alkyl groups, polyorganosiloxane chains possibly containing one or more oxygen, sulfur and/or nitrogen atoms, the groups X, which may be identical or different, represent a linear or branched $C_1$ to $C_{30}$ alkylenediyl group, which may contain in its chain one or more oxygen and/or nitrogen atoms;

Y is a saturated or unsaturated C1 to C50 linear or branched alkylene, arylene, cycloalkylene, alkylarylene or arylalkylene divalent group, which may comprise one or more oxygen, sulfur and/or nitrogen atoms, and/or may bear as substituent one of the following atoms or groups of atoms: fluorine, hydroxyl, $C_3$ to $C_8$ cycloalkyl, $C_1$ to $C_{40}$ alkyl, C5 to C10 aryl, phenyl optionally substituted with 1 to 3 C1 to C3 alkyl, C1 to C3 hydroxyalkyl and C1 to C6 aminoalkyl groups, or Y represents a group corresponding to the formula:

$$R^5-T\diagup_{\diagdown}$$

in which:

T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and R5 represents a linear or branched $C_1$-$C_{50}$ alkyl group or a polyorganosiloxane chain, possibly comprising one or more ester, amide, urethane, thiocarbamate, urea, thiourea and/or sulfonamide groups, which may possibly be linked to another chain of the polymer;

the groups G, which may be identical or different, represent divalent groups chosen from:

$$-\overset{\text{O}}{\underset{\|}{C}}-O-; \quad -O-\overset{\|}{\underset{\text{O}}{C}}-; \quad -N(R^6)-\overset{\|}{\underset{\text{O}}{C}}-;$$

$$-\overset{\text{O}}{\underset{\|}{C}}-N(R^6)-; \quad -N(R^6)-SO_2-;$$

$$-SO_2-N(R^6)-; \quad -N(R^6)-\overset{\|}{\underset{\text{O}}{C}}-O-;$$

$$-O-\overset{\|}{\underset{\text{O}}{C}}-N(R^6)-; \quad -N(R^6)-\overset{\|}{\underset{\text{S}}{C}}-O-;$$

$$-O-\overset{\|}{\underset{\text{S}}{C}}-N(R^6)-; \quad -N(R^6)-\overset{\|}{\underset{\text{O}}{C}}-N(R^6)-\quad \text{et}$$

$$N(R^6)-\overset{\|}{\underset{\text{S}}{C}}-N(R^6)-\quad -N(R^6)-\overset{\|}{\underset{\text{O}}{C}}-\overset{\|}{\underset{\text{O}}{C}}-N(R^6);$$

$$-NH-\overset{\|}{\underset{\text{NH}}{C}}-NH-; \quad \text{et}$$

$$-NH-\overset{\|}{\underset{\text{NH}}{C}}-NH-\overset{\|}{\underset{\text{NH}}{C}}-NH-$$

in which R6 represents a hydrogen atom or a linear or branched $C_1$ to $C_{20}$ alkyl group, n is an integer ranging from 2 to 500 and preferably from 2 to 200, and m is an integer ranging from 1 to 1000, preferably from 1 to 700 and better still from 6 to 200.

According to one embodiment variant, 80% of the groups R1, R2, R3 and R4 of the polymer may be chosen especially from methyl, ethyl, phenyl and 3,3,3-trifluoropropyl groups.

According to another embodiment variant, Y may represent various divalent groups, optionally also comprising one or two free valencies to establish bonds with other units of the polymer or copolymer. Y may especially represent a group chosen from:

a) linear $C_1$ to $C_{20}$ and especially $C_1$ to $C_{10}$ alkylene groups;

b) $C_{30}$ to $C_{56}$ branched alkylene groups possibly comprising rings and unconjugated unsaturations, c) $C_5$-$C_6$ cycloalkylene groups;

d) phenylene groups optionally substituted with one or more $C_1$ to $C_{40}$ alkyl groups, e) $C_1$ to $C_{20}$ alkylene groups comprising from 1 to 5 amide groups, f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups, g) polyorganosiloxane chains of formula:

$$R^1-\overset{R^2}{\underset{R^4}{\overset{|}{Si}}}-O-\left[\overset{R^1}{\underset{R^3}{\overset{|}{Si}}}-O\right]_m-\overset{R^2}{\underset{R^4}{\overset{|}{Si}}}-T\diagup_{\diagdown}$$

in which R1, R2, R3 and R4, T and m are as defined above; and h) polyorganosiloxane chains of formula:

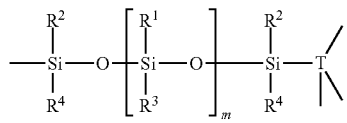

The polyorganosiloxanes of the second family may be polymers comprising at least one unit corresponding to the second formula below:

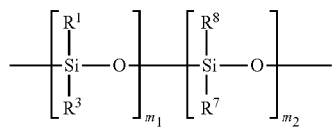

in which:

R1 and R3, which may be identical or different, are as defined above for the preceding formula;

R7 represents a group as defined above for R1 and R3, or represents the group of formula —X-G-R9 in which X and G are as defined above for the preceding formula and R9 represents a hydrogen atom or a linear, branched or cyclic, saturated or unsaturated $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups;

R8 represents a group of formula —X-G-R9 in which X, G and R9 are as defined above;

m1 is an integer ranging from 1 to 998; and m2 is an integer ranging from 2 to 500.

According to the invention, the silicone polyamide used as structuring agent may be a homopolymer, i.e. a polymer comprising several identical units, in particular units according to the formulae defined above.

According to the invention, it is also possible to use a silicone polyamide consisting of a copolymer comprising several different units according to the first formula above, i.e. a polymer in which at least one of the groups R1, R2, R3, R4, X, G, Y, m and n is different in one of the units. The copolymer may also be formed from several units according to the second formula above, in which at least one of the groups R1, R3, R7, R8, m1 and m2 is different in at least one of the units.

It is also possible to use a copolymer comprising at least one unit according to the first formula and at least one unit according to the second formula, the units according to the first formula and the units according to the second formula possibly being identical to or different from each other.

According to one variant of the invention, it is also possible to use a silicone polyamide of copolymer type also comprising at least one hydrocarbon-based unit comprising two groups capable of establishing hydrogen interactions chosen from ester, amide, sulfonamide, carbamate, thiocarbamate, urea and thiourea groups, and combinations thereof. These copolymers may be block copolymers or grafted copolymers.

According to one embodiment variant, the groups capable of establishing hydrogen interactions are amide groups of formulae —C(O)NH— and —HN—C(O)—. In this case, the gelling agent may be, for example, a polymer comprising at least one unit according to the third or fourth formula below:

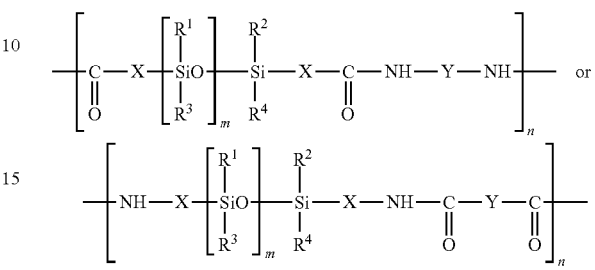

in which R1, R2, R3, R4, X, Y, m and n are as defined above.

In the polyamides according to the third and fourth formulae presented above:

m is especially in the range from 1 to 700, or even from 15 to 500 and better still from 15 to 45, and n is in particular in the range from 1 to 500, especially from 1 to 100 and better still from 4 to 25, X is especially a linear or branched alkylene chain containing from 1 to 30 carbon atoms and in particular 3 to 10 carbon atoms, and Y is especially a linear or branched alkylene chain or a chain that may comprise rings and/or unsaturations, containing from 1 to 40 carbon atoms, in particular from 1 to 20 carbon atoms and better still from 2 to 6 carbon atoms, in particular 6 carbon atoms.

In the third and fourth formulae presented above, the alkylene group representing X or Y may optionally contain in its alkylene part at least one of the following elements:

1) 1 to 5 amide, urea or carbamate groups, 2) a $C_5$ or $C_6$ cycloalkyl group, and 3) a phenylene group optionally substituted with 1 to 3 identical or different $C_1$ to $C_3$ alkyl groups.

In the third and fourth formulae presented above, the alkylene groups may also be substituted with at least one element chosen from the group consisting of:

a hydroxyl group, a $C_3$ to $C_8$ cycloalkyl group, one to three $C_1$ to $C_{40}$ alkyl groups, a phenyl group optionally substituted with one to three $C_1$ to $C_3$ alkyl groups, a $C_1$ to $C_3$ hydroxyalkyl group, and a $C_1$ to $C_6$ aminoalkyl group. In the third and fourth formulae presented above, Y may also represent:

in which R5 represents a polyorganosiloxane chain, and T represents a group of formula:

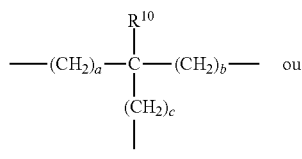   ou

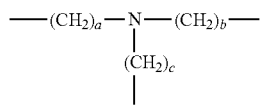

in which a, b and c are, independently, integers ranging from 1 to 10, and R10 is a hydrogen atom or a group such as those defined for R1, R2, R3 and R4.

In the third and fourth formulae presented above, R1, R2, R3 and R4 especially represent, independently, a linear or branched $C_1$ to $C_{40}$ alkyl group, in particular a $CH_3$, $C_2H_5$, n-$C_3H_7$ or isopropyl group, a polyorganosiloxane chain or a phenyl group optionally substituted with one to three methyl or ethyl groups.

As has been seen previously, the polymer may also comprise identical or different units according to the third or fourth formula presented above.

Thus, the polymer may be a silicone polyamide containing several units according to the third or fourth formula presented above, of different lengths, or a polyamide corresponding to the fifth formula below:

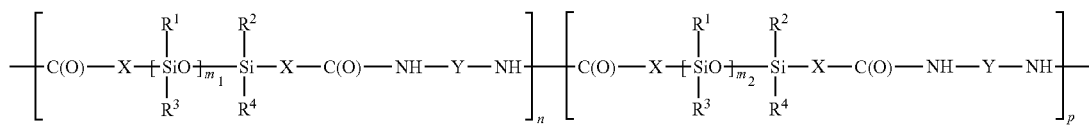

in which X, Y, n, R1 to R4 have the meanings given above, m1 and m2, which are different, are chosen in the range from 1 to 1000, and p is an integer ranging from 2 to 300.

In this formula, the units may be structured to form either a block copolymer, or a random copolymer or an alternating copolymer. In this copolymer, the units may be not only of different lengths, but also of different chemical structures, for example containing different groups Y. In this case, the copolymer may correspond to the sixth formula:

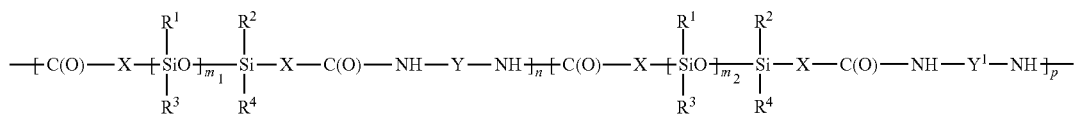

in which R1 to R4, X, Y, m1, m2, n and p have the meanings given above and Y1 is different from Y but chosen from the groups defined for Y. As previously, the various units may be structured to form either a block copolymer, or a random copolymer or an alternating copolymer.

According to one embodiment of the invention, the gelling silicone polyamide may also consist of a grafted copolymer. Thus, the polyamide containing silicone units may be grafted and optionally crosslinked with silicone chains containing amide groups. Such polymers may be synthesized with trifunctional amines.

In this case, the copolymer may comprise at least one unit according to the seventh formula below:

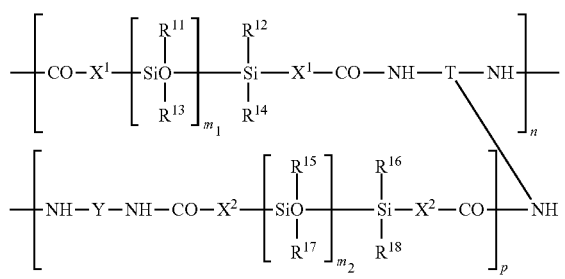

in which X1 and X2, which may be identical or different, have the meaning given for X in the first formula above, n is as defined in the first formula above, Y and T are as defined in the first formula above, R11 to R18 are groups chosen from the same group as the groups R1 to R4, m1 and m2 are numbers in the range from 1 to 1000, and p is an integer ranging from 2 to 500.

In the seventh formula presented above, in particular:
p is in the range from 1 to 25 and better still from 1 to 7,
R11 to R18 are methyl groups,
T corresponds to one of the following formulae:

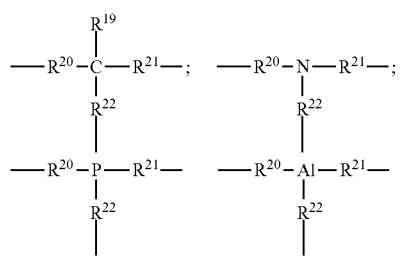

in which R19 is a hydrogen atom or a group chosen from the groups defined for R1 to R4, and R20, R21 and R22 are, independently, linear or branched alkylene groups, T preferably corresponds in particular to the formula:

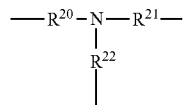

especially with R20, R21 and R22 representing —$CH_2$—$CH_2$—,
m1 and m2 are in the range from 15 to 500 or even from 15 to 45,
X1 and X2 represent —$(CH_2)_{10}$—, and
Y represents —$CH_2$—.

These polyamides containing a grafted silicone unit according to the seventh formula presented above may be copolymerized with silicone polyamides according to the second formula to form block copolymers, alternating copolymers or random copolymers. The weight percentage of grafted silicone units according to the seventh formula in the copolymer may range from 0.5% to 30% by weight.

According to one embodiment, the siloxane units may be in the main chain or backbone of the polymer, but they may also be present in grafted chains or side chains. In the main chain, the siloxane units may be in the form of segments as described above. In the side or grafted chains, the siloxane units may appear individually or in segments.

According to one embodiment of the invention, the siloxane-based polyamides may especially be:
polyamides according to the third formula presented above in which m is from 15 to 50;
mixtures of two or more polyamides in which at least one polyamide has a value of m in the range from 15 to 50 and at least one polyamide has a value of m in the range from 30 to 50; polymers according to the fifth formula described above with m1 chosen in the range from 15 to 50 and m2 chosen in the range from 30 to 500 with the part corresponding to m1 representing 1% to 99% by weight relative to the total weight of the polyamide and the part corresponding to m2 representing 1% to 99% by weight relative to the total weight of the polyamide;
polyamide blends according to the third formula described above, combining:
1) 80% to 99% by weight of a polyamide in which n is equal to 2 to 10 and in particular 3 to 6, and
2) 1% to 20% of a polyamide in which n is in the range from 5 to 500 and in particular from 6 to 100;
polyamides corresponding to the sixth formula presented above in which at least one of the groups Y and Y1 contains at least one hydroxyl substituent;
polyamides according to the third formula synthesized with at least part of an activated diacid (diacid chloride, dianhydride or diester) instead of the diacid;
polyamides according to the third formula in which X represents —$(CH_2)_3$— or —$(CH_2)_{10}$—; and
polyamides according to the third formula in which the polyamides end with a monofunctional chain chosen from the group consisting of monofunctional amines, monofunctional acids, monofunctional alcohols, including fatty acids, fatty alcohols and fatty amines, for instance octylamine, octanol, stearic acid and stearyl alcohol.

According to one embodiment of the invention, the ends of the polymer chains may end with:
a $C_1$ to $C_{50}$ alkyl ester group by introducing during the synthesis a $C_1$ to $C_{50}$ monoalcohol,
a $C_1$ to $C_{50}$ alkylamide group by taking as stopper a monoacid if the silicone contains α,ω-diamino, or a monoamine if the silicone contains α,ω-dicarboxylic acid.

According to one embodiment variant of the invention, it is possible to use a copolymer of silicone polyamide and of hydrocarbon-based polyamide, i.e. a copolymer comprising units according to the third or fourth formula and hydrocarbon-based polyamide units. In this case, the polyamide-silicone units may be located at the ends of the hydrocarbon-based polyamide.

Polyamide-based gelling agents containing silicones may be produced by silyl amidation of polyamides based on fatty acid dimer. This approach involves the reaction of free acid sites existing on a polyamide as end sites, with oligosiloxane-monoamines and/or oligosiloxane-diamines (amidation reaction), or alternatively with oligosiloxane alcohols or oligosiloxane diols (esterification reaction). The esterification reaction requires the presence of acidic catalysts, as is known in the art. It is desirable for the polyamide containing free acid sites, used for the amidation or esterification reaction, to have a relatively high number of acid end groups (for example polyamides with high acid numbers, for example from 15 to 20).

For the amidation of the free acid sites of the hydrocarbon-based polyamides, siloxane diamines with 1 to 300, more particularly 2 to 50 and better still 2, 6, 9.5, 12, 13.5, 23 or 31 siloxane groups may be used for the reaction with hydrocarbon-based polyamides based on fatty acid dimers. Siloxane diamines containing 13.5 siloxane groups are preferred, and the best results are obtained with the siloxanediamine containing 13.5 siloxane groups and polyamides with high numbers of carboxylic acid end groups.

The reactions may be performed in xylene to extract the water produced from the solution by azeotropic distillation, or at higher temperatures (about 180 to 200° C.) without solvent. Typically, the amidation efficacy and the reaction rates decrease when the siloxane diamine is longer, i.e. when the number of siloxane groups is higher. Free amine sites may be blocked after the initial amidation reaction of the diaminosiloxanes by reacting them either with an acidic siloxane or an organic acid such as benzoic acid.

For the esterification of the free acid sites on the polyamides, this may be performed in boiling xylene with about 1% by weight, relative to the total weight of the reagents, of para-toluenesulfonic acid as catalyst.

These reactions performed on the carboxylic acid end groups of the polyamide lead to the incorporation of silicone units only at the ends of the polymer chain.

By way of example, mention will be made of DC2-8178 Gellant and DC2-8179 Gellant from Dow Corning.

4) Saccharide or Polysaccharide Mono- or Polyalkyl Esters

Among the saccharide or polysaccharide monoalkyl or polyalkyl esters that are suitable for use in the invention, mention may be made of dextrin or inulin alkyl or polyalkyl esters.

It may especially be a dextrin mono- or polyester of at least one fatty acid corresponding especially to the following formula:

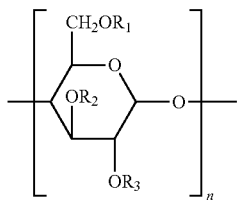

in which:
n is an integer ranging from 3 to 200, especially ranging from 20 to 150 and in particular ranging from 25 to 50,
the radicals R1, R2 and R3, which may be identical or different, are chosen from hydrogen and an acyl group (R—CO—) in which the radical R is a linear or branched, saturated or unsaturated hydrocarbon-based group containing from 7 to 29, in particular from 7 to 21, especially from 11 to 19, more particularly from 13 to 17, or even 15, carbon atoms, with the proviso that at least one of the said radicals R1, R2 or R3 is other than hydrogen.

In particular, R1, R2 and R3 may represent hydrogen or an acyl group (R—CO—) in which R is a hydrocarbon-based radical as defined above, with the proviso that at least two of the said radicals R1, R2 or R3 are identical and other than hydrogen.

The radicals R1, R2 and R3 may all contain an acyl group (R—CO), which is identical or different and especially identical.

In particular, n mentioned above advantageously ranges from 25 to 50 and is especially equal to 38 in the general formula of the saccharide ester that may be used in the present invention.

In particular, when the radicals R1, R2 and/or R3, which may be identical or different, contain an acyl group (R—CO), these radicals may be chosen especially from caprylic, capric, lauric, myristic, palmitic, stearic, arachic, behenic, isobutyric, isovaleric, 2-ethylbutyric, ethylmethylacetic, isoheptanoic, 2-ethylhexanoic, isononanoic, isodecanoic, isotridecanoic, isomyristic, isopalmitic, isostearic, isoarachic, isohexanoic, decenoic, dodecenoic, tetradecenoic, myristoleic, hexadecenoic, palmitoleic, oleic, elaidic, asclepinic, gondoleic, eicosenoic, sorbic, linoleic, linolenic, punicic, stearidonic, arachidonic and stearolic radicals, and mixtures thereof.

Preferably, at least one dextrin palmitate is used as fatty acid ester of dextrin. This ester may be used alone or as a mixture with other esters.

Advantageously, the fatty acid ester of dextrin has a degree of substitution of less than or equal to 2.5, especially ranging from 1.5 to 2.5 and preferably from 2 to 2.5 on the basis of one glucose unit. The weight-average molecular weight of the dextrin ester may in particular be from 10 000 to 150 000, especially from 12 000 to 100 000 and even from 15 000 to 80000.

Dextrin esters, in particular dextrin palmitates, are commercially available under the name Rheopearl TL or Rheopearl KL by the company Chiba Flour.

5) N-acylamino Acid Amide Derivatives

The N-acylamino acid amides that may be used are, for example, diamides from the combination of an N-acylamino acid with amines comprising from 1 to 22 carbon atoms, such as those described in document FR 2 281 162. They are, for example, alkylglutamic acid amide derivatives such as the laurylglutamic acid dibutylamide sold by the company Ajinomoto under the name Gelling Agent GP-1, or alternatively the 2-ethylhexylglutamic acid dibutylamide sold by the company Ajinomoto under the name Gelling Agent GA-01.

6) Copolymers Comprising an Alkylene or Styrene Block

The copolymers may have a comb or the block structure of diblock, triblock, multiblock and/or radial or star type and may comprise at least two thermodynamically incompatible segments.

The structuring agent may comprise, for example, a styrene segment as described in patent applications EP 0 497 144, WO 98/42298, U.S. Pat. Nos. 6,225,690, 6,174,968 and 6,225,390, an ethylene/butylene segment or an ethylene/propylene segment as described in patent applications U.S. Pat. Nos. 6,225,690, 6,174,968 and 6,225,390, a butadiene segment, an isoprene segment, a polyvinyl segment, for instance polyalkyl (meth)acrylate or polyvinyl alcohol or polyvinyl acetate, a silicone segment as described in U.S. Pat. Nos. 5,468,477 and 5,725,882, or a combination of these segments.

A diblock copolymer is usually defined as being of A-B type in which a hard segment (A) is followed by a soft segment (B).

A triblock copolymer is usually defined as being of A-B-A type or as a ratio of a hard segment, a soft segment and a hard segment.

A multiblock, radial or star copolymer may comprise any type of combination of hard segments and soft segments, with the proviso that the characteristics of the hard segments and of the soft segments are conserved.

An example of hard segments of block copolymers that may be mentioned is styrene, and examples of soft segments of block copolymers that may be mentioned include ethylene, propylene and butylene, and a combination thereof.

The triblock copolymers, and especially those of polystyrene/polyisoprene or polystyrene/polybutadiene type, which are suitable for use in the invention may be those sold under the reference Luvitol HSB by the company BASF. Mention may also be made of triblock copolymers of polystyrene/copoly(ethylene-propylene) or polystyrene/copoly(ethylene-butylene) type, such as those sold under the reference Kraton by the company Shell Chemical Co., or under the reference Gelled Permethyl 99 A by the company Penreco. Such triblock copolymers are particularly preferred according to the invention.

As a further example of block copolymers that may be suitable for use in the present invention, mention may also be made of the block copolymers sold under the reference Versagel by the company Penreco, those sold under the reference Kraton by the company Shell and those sold under the reference Gel Base by the company Brooks Industries.

Among the fatty-phase thickening polymers, polymers bearing in the backbone at least one crystallizable block are preferred.

The aqueous-phase or fatty-phase thickening polymers may be used alone or as mixtures in all proportions.

According to one particular embodiment of the invention, the thickening polymer(s) are chosen from aqueous-phase thickening polymers.

According to one preferred embodiment, the thickening polymer(s) present in the composition in accordance with the invention are derived from sugars. In one variant of the invention, the thickening polymer(s) are chosen from xanthan gums.

The anionic or nonionic thickening polymer(s) are present in the composition according to the invention in a content ranging from 0.1% to 10% by weight and preferably from 1% to 5% by weight relative to the total weight of the composition.

According to one particular embodiment of the invention, the sulfinic acid derivatives of formula (I) and/or cosmetically acceptable salts thereof/anionic or nonionic thickening polymers weight ratio ranges from 0.2 to 20 and preferably from 2 to 15.

The stripping composition in accordance with the invention may also contain various adjuvants conventionally used in stripping compositions, such as anionic, cationic, nonionic, amphoteric or zwitterionic surfactants or mixtures thereof, nonionic, anionic, amphoteric, zwitterionic or cationic conditioning polymers or mixtures thereof, preferably cationic or amphoteric substantive polymers, penetrants, sequestrants, fragrances, dispersants, volatile or non-volatile, modified or unmodified silicones, film-forming agents, ceramides, preserving agents, opacifiers, mineral or plant oils, waxes and vitamins.

Needless to say, a person skilled in the art will take care to select this or these optional additional compound(s) such that the advantageous properties intrinsically associated with the stripping composition that is useful in the invention are not, or are not substantially, adversely affected by the envisaged addition(s).

The composition according to the invention generally comprises water or a mixture of water and at least one organic solvent. Examples of organic solvents that may be mentioned include $C_1$-$C_4$ lower alkanols, such as ethanol and isopropanol; glycerol; glycols and glycol ethers, for instance 2-butoxyethanol, propylene glycol, dipropylene glycol, hexylene glycol, propylene glycol monomethyl ether, diethylene glycol monomethyl ether and monoethyl ether, and also aromatic alcohols, for instance benzyl alcohol or phenoxyethanol, similar products and mixtures thereof.

The solvents may then be present in proportions preferably of between 0.5% and 20% and more particularly between 2% and 10% by weight relative to the total weight of the stripping composition.

According to one particular embodiment, the composition according to the invention is aqueous, i.e. it comprises water in a proportion preferably ranging from 10% to 90% by weight, preferentially from 20% to 90% by weight and better still from 40% to 75% by weight relative to the total weight of the composition.

The pH of the stripping composition in accordance with the invention, if it is aqueous, generally ranges from 2 to 11, preferably from 2 to 7 and better still from 2 to 5. It is adjusted by means of acidifying or basifying agents, which are generally present in the composition in proportions preferably of between 0.01% and 30% by weight relative to the total weight of the stripping composition.

Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

Among the basifying agents, examples that may be mentioned include aqueous ammonia, alkali metal silicates, alkali metal carbonates, alkanolamines, such as mono-, di- and triethanolamines, 2-methyl-2-amino-1-propanol and derivatives thereof, sodium hydroxide, potassium hydroxide and the compounds of formula (X) below:

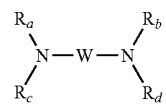

(X)

in which W is a propylene residue optionally substituted with a hydroxyl group or a $C_1$-$C_4$ alkyl radical; $R_a$, $R_b$, $R_c$ and $R_d$, which may be identical or different, represent a hydrogen atom or a $C_1$-$C_4$ alkyl or $C_1$-$C_4$ hydroxyalkyl radical.

The stripping composition that is useful in the invention may be in various forms, such as in the form of solutions, emulsions, creams or gels, optionally pressurized in the form of mousses, or in any other form that is suitable for stripping the artificial colour of keratin fibres, and in particular human keratin fibres such as the hair.

The composition of the invention may result from the mixing of at least two compositions.

In particular, the compositions intended for bleaching the hair using reducing agents of the invention may be in the form of ready-to-use compositions formed from anhydrous products (powders) or creams or gels containing the reducing agent(s), which are mixed at the time of use with an aqueous composition containing a pH agent.

The composition according to the invention is intended to be applied in unmodified form to keratin fibres, i.e. it may be stored in unmodified form before use or may result from the extemporaneous mixing of two or more compositions.

According to one particular embodiment of the invention, the composition in accordance with the invention is derived from the mixing of an aqueous or anhydrous composition (A) comprising the sulfinic acid derivative(s) of formula (I) as defined above and of an aqueous composition (B), the anionic or nonionic fixing polymer(s) possibly being in one of the compositions (A) or (B) or in both of them.

According to one preferred embodiment of the invention, composition (A) is anhydrous.

When composition (A) is anhydrous, it may furthermore comprise at least one inert organic liquid phase.

Reference may be made in this case also to the description giving the definition of the inert liquid phases and of the lists of compounds that are appropriate in this respect.

Preferably, the inert organic liquid phase is preferably from the polydecenes of formula $C_{10n}H_{[(20n)+2]}$ in which n ranges from 3 to 9 and preferably from 3 to 7, and esters of fatty alcohols or of fatty acids, and mixtures thereof.

According to one particular embodiment of the invention, the content of inert organic liquid phase in the anhydrous composition (A) ranges from 5% to 60% by weight, preferably from 10% to 50% by weight and even more preferentially from 15% to 45% by weight relative to the weight of the anhydrous paste.

The anhydrous composition (A) that is useful in the context of the invention may be in powder or paste form. Advantageously, the composition of the invention is in the form of a paste.

According to one preferred embodiment of the invention, the anionic or nonionic fixing polymer(s) are present in the composition comprising the sulfinic acid derivative(s) of formula (I) as defined above.

According to one particular embodiment of the invention, the mixing ratio between the composition (A) and composition (B) ranges from 0.1 to 10, preferentially from 0.2 to 4 and better still from 0.2 to 1.

In particular, the mixing ratio between the composition (A) and composition (B) and the pH of the aqueous composition(s) are adjusted such that the pH of the mixture between compositions (A) and (B) preferably ranges from 2 to 5.

A subject of the present invention is also a process for stripping the artificial colour from keratin fibres, in which a composition as defined above is applied to the said keratin fibres for a leave-on time that is sufficient to strip the artificial colour from the keratin fibres.

The application temperature of the stripping composition is generally between 20 and 250° C. and preferably between 20 and 80° C.

The leave-on time that is sufficient to strip the artificial colour from keratin fibres is generally between 1 minute and 120 minutes and preferably between 5 minutes and 60 minutes.

The application conditions, such as the application temperature and the leave-on time, the pH of the stripping composition and the amount of sulfinic acid derivatives of formula (I) as defined above, depend on the amount and nature of the artificial dyes to be removed, and also on the desired degree of bleaching.

A subject of the present invention is also a first multi-compartment device for stripping the artificial colour of keratin fibres dyed with oxidation dyes and/or direct dyes, comprising, in a first compartment, the anhydrous or aqueous composition (A), and, in a second compartment, the aqueous composition (B), the latter composition comprising at least one organic acid other than the compounds of formula (I) and with a pKa of less than or equal to 4 when the composition (A) is aqueous, compositions (A) and (B) being as defined above. It should be noted that composition (B) may similarly comprise at least one organic acid different from the compounds of formula (I) and with a pKa of less than or equal to 4 when composition (A) is anhydrous.

A subject of the present invention is also a second multi-compartment device for dyeing and then stripping the artificial colour of keratin fibres, comprising a third compartment containing a dye composition and optionally a fourth compartment containing an oxidizing composition.

A subject of the present invention is also a third multi-compartment device for dyeing and then stripping the artificial colour of keratin fibres, comprising a first compartment containing a composition comprising at least one oxidation dye precursor and/or at least one direct dye and a second compartment containing a stripping composition comprising, in a cosmetically acceptable medium, at least one sulfinic acid derivative of formula (I) defined previously, and salts thereof, and at least one thickener chosen from anionic polymers and nonionic polymers; and optionally a third compartment containing an oxidizing composition.

According to one particular embodiment of the invention, the composition for dyeing keratin fibres is an oxidation dye composition that comprises at least one oxidation base and/or at least one coupler.

The oxidation bases are chosen from the oxidation bases conventionally used in oxidation dyeing. By way of example, these oxidation bases are chosen from para-phenylenediamines, double bases, para-aminophenols, ortho-aminophenols and heterocyclic bases, and the addition salts thereof.

Among the para-phenylenediamines, mention may be made of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloro-aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-β,γdihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylene-diamine and 2-methyl-1-N-β-hydroxyethyl-para-phenylenediamine, and the addition salts thereof with an acid.

Among the double bases, mention may be made of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid.

Among the para-aminophenols, mention may be made of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethyl-aminomethyl)phenol, and the addition salts thereof with an acid.

Among the ortho-aminophenols, mention may be made of 2-aminophenol, 2-amino-1-hydroxy-5-methylbenzene, 2-amino-1-hydroxy-6-methylbenzene and 5-acetamido-2-aminophenol, and the addition salts thereof with an acid.

Among the heterocyclic bases, mention may be made of pyridine derivatives, and more particularly the compounds described, for example, in patents GB 1 026 978 and GB 1 153 196, for instance 2,5-diaminopyridine, 2-(4-methoxyphenyl)amino-3-aminopyridine, 2,3-diamino-6-methoxypyridine, 2-(β-methoxyethylamino-3-amino-6-methoxypyridine and 3,4-diaminopyridine, and the addition salts thereof with an acid.

Among the heterocyclic bases, mention may also be made of pyrimidine derivatives, and more particularly the compounds described, for example, in German patents DE 2 359 399 or Japanese patents JP 88-169 571 and JP 91-10659 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)-(2-hydroxyethyl)amino]ethanol; 2-[(7-aminopyrazolo[1,5-a]pyrimidin-3-yl)(2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2, 5, N7, N7-tetramethylpyrazolo[1,5-a]pyrimidine-3,7-diamine; 3-amino-5-methyl-7-imidazolylpropylaminopyrazolo[1,5-a]pyrimidine; and the addition salts thereof and tautomeric forms thereof, when a tautomeric equilibrium exists, and the addition salts thereof with an acid.

Among the heterocyclic bases, mention may also be made of pyrazole derivatives, such as the compounds described in patents DE 3 843 892 and DE 4 133 957 and patent applications WO 94/08969, WO 94/08970, FR-A-2 733 749 and DE 195 43 988. Examples that may be mentioned include 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)-pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole and 4,5-diamino-1-(β-methoxyethyl)pyrazole, and the addition salts thereof with an acid.

The couplers are chosen from the couplers conventionally used in oxidation dyeing. By way of example, these couplers are chosen from meta-phenylenediamines, meta-aminophenols, meta-diphenols, naphthalene-based couplers and heterocyclic couplers, and the addition salts thereof.

Among the couplers, mention may be made especially of 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 1-acetoxy-2-methylnaphthalene, 2-methyl-1-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole and 2,6-dimethylpyrazolo[1,5-b]-1,2,4-triazole, and the addition salts thereof with an acid.

In general, the addition salts of the oxidation bases and couplers that may be used in the context of the invention are especially chosen from the addition salts with an acid, such as the hydrochlorides, hydrobromides, sulfates, citrates, succinates, tartrates, lactates, tosylates, benzenesulfonates, phosphates and acetates, and the addition salts with a base, such as sodium hydroxide, potassium hydroxide, ammonia, amines or alkanolamines.

The oxidation base(s) are generally present in the oxidation dye composition in an amount of between 0.0005% and 12% by weight approximately and preferably between 0.005% and 8% by weight approximately relative to the total weight of the dye composition.

The coupler(s) are generally present in the oxidation dye composition in an amount of between 0.0001% and 15% by weight approximately and preferably between 0.001% and 10% by weight approximately relative to the total weight of the dye composition.

According to another particular embodiment of the invention, the composition for dyeing keratin fibres is a direct dye composition that comprises at least one direct dye which may be chosen especially from nitrobenzene dyes, azo direct dyes, methine direct dyes, quinone direct dyes, azine direct dyes, triarylmethane direct dyes, indoamine direct dyes and natural direct dyes. These direct dyes may be of nonionic, anionic or cationic nature.

Among the benzenic direct dyes, mention may be made of 1,4-diamino-2-nitrobenzene, 1-amino-2-nitro-4-(β-hydroxyethylamino)benzene, 1-amino-2-nitro-4-bis(β-hydroxyethyl)aminobenzene, 1,4-bis(β-hydroxyethylamino)-2-nitrobenzene, 1-β-hydroxyethylamino-2-nitro-4-bis(β-hydroxyethylamino)benzene, 1-β-hydroxyethylamino-2-nitro-4-aminobenzene, 1-β-hydroxyethylamino-2-nitro-4-(ethyl)(β-hydroxyethyl)aminobenzene, 1-amino-3-methyl-4-β-hydroxyethylamino-6-nitrobenzene, 1-amino-2-nitro-4-β-hydroxyethylamino-5-chlorobenzene, 1,2-diamino-4-nitrobenzene, 1-amino-2-β-hydroxyethylamino-5-nitrobenzene, 1,2-bis(β-hydroxyethylamino)-4-nitrobenzene, 1-amino-2-[tris-(hydroxymethyl)methylamino]-5-nitrobenzene, 1-hydroxy-2-amino-5-nitrobenzene, 1-hydroxy-2-amino-4-nitrobenzene, 1-hydroxy-3-nitro-4-aminobenzene, 1-hydroxy-2-amino-4,6-dinitrobenzene, 1-β-hydroxyethyloxy-2-β-hydroxyethylamino-5-nitrobenzene, 1-methoxy-2-β-hydroxyethylamino-5-nitrobenzene, 1-3-hydroxyethyloxy-3-methylamino-4-nitrobenzene, 1-β,γ-dihydroxypropyloxy-3-methylamino-4-nitrobenzene, 1-β-hydroxyethylamino-4-β,γ-dihydroxypropyloxy-2-nitrobenzene, 1-β,γ-dihydroxypropyl-amino-4-trifluoromethyl-2-nitrobenzene, 1-β-hydroxyethylamino-4-trifluoromethyl-2-nitrobenzene, 1-β-hydroxyethylamino-3-methyl-2-nitrobenzene, 1-β-aminoethyl-amino-5-methoxy-2-nitrobenzene, 1-hydroxy-2-chloro-6-ethylamino-4-nitrobenzene, 1-hydroxy-2-chloro-6-amino-4-nitrobenzene, 1-hydroxy-6-[bis(β-hydroxyethyl)amino]-3-nitrobenzene, 1-β-hydroxyethylamino-2-nitrobenzene and 1-hydroxy-4-β-hydroxyethylamino-3-nitrobenzene.

Among the azo direct dyes, mention may be made of the cationic azo dyes described in patent applications WO-95/15144, WO-95/01772 and EP-0 714 954, the content of which forms an integral part of the invention.

Among these compounds, mention may be made most particularly of 1,3-dimethyl-2-[[4-(dimethylamino)phenyl]azo]-1H-imidazolium chloride, 1,3-dimethyl-2-[(4-aminophenyl)azo]-1H-imidazolium chloride and 1-methyl-4-[(methylphenylhydrazono)methyl]pyridinium methyl sulfate.

Among the azo direct dyes, mention may also be made of the following dyes, described in the Colour Index International 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Mention may also be made of 1-(4'-aminodiphenylazo)-2-methyl-4-bis(β-hydroxyethyl)aminobenzene and 4-hydroxy-3-(2-methoxyphenylazo)-1-naphthalenesulfonic acid.

Among the quinone direct dyes that may be mentioned are the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds: 1-N-methylmorpholiniumpropylamino-4-hydroxyanthraquinone, 1-aminopropylamino-4-methylaminoanthraquinone, 1-aminopropylaminoanthraquinone, 5-β-hydroxyethyl-1,4-diaminoanthraquinone, 2-aminoethylaminoanthraquinone, 1,4-bis(β,γ-dihydroxypropylamino)anthraquinone.

Among the azine dyes that may be mentioned are the following compounds: Basic Blue 17, Basic Red 2.

Among the triarylmethane dyes, mention may be made of the following compounds: Basic Green 1, Acid Blue 9, Basic Violet 3, Basic Violet 14, Basic Blue 7, Acid Violet 49, Basic Blue 26, Acid Blue 7.

Among the indoamine dyes, mention may be made of the following compounds: 2β-hydroxyethlyamino-5-[bis(β-4'-hydroxyethyl)amino]anilino-1,4-benzoquinone, 2β-hydroxyethylamino-5-(2'-methoxy-4'-amino)anilino-1,4-benzoquinone, 3-N-(2'-chloro-4'-hydroxy)phenylacetylamino-6-methoxy-1,4-benzoquinoneimine, 3-N(3'-chloro-4'-methylamino)phenylureido-6-methyl-1,4-benzoquinoneimine and 3-[4'-N-(ethylcarbamylmethyl)amino]phenylureido-6-methyl-1,4-benzoquinoneimine.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes and in particular henna-based poultices or extracts, may also be used.

The direct dye(s) are generally present in an amount of between 0.001% and 20% by weight, approximately and even more preferably approximately between 0.005% and 10% by weight approximately relative to the total weight of the dye composition.

According to another particular embodiment of the invention, the dye composition is a composition that comprises at least one oxidation base, optionally at least one coupler, and at least one direct dye.

Preferably, the process for stripping keratin fibres, and in particular human keratin fibres such as the hair, of the invention applies to fibres dyed with oxidation dyes.

The multi-compartment device in accordance with the invention may also comprise a fourth compartment containing an oxidizing composition.

The examples that follow serve to illustrate the invention without, however, being limiting in nature.

EXAMPLES A

I) Dyeing Step 1-g locks of natural, permanent-waved or non-permanent-waved hair containing 90% grey hairs are dyed with Majirouge Mix Plus Absolu Nuance Rouge (L'Oréal Professionnel) or with Movida 45 (Garnier).

Majirouge Mix Plus Absolu Nuance Rouge Dye Composition:
p-phenylenediamine: 0.25 g %
resorcinol: 0.009 g %
p-aminophenol: 0.25 g %
4-amino-2-hydroxybenzene: 0.26 g %
2-methyl-5-hydroxyethylaminophenol: 0.82 g %

Movida 45 Dye Composition:
p-toluenediamine: 1.9 g %
resorcinol: 0.7 g %
2-(β-hydroxyethyloxy)-p-phenylenediamine dihydrochloride: 0.06 g %
m-aminophenol: 0.08 g %
2-methylresorcinol: 1.1 g %

10 g of each of the dye compositions are mixed with 15 g (for Majirouge Mix Plus Absolu Nuance Rouge) or 20 g (for Movida 45) of a 20-volumes hydrogen peroxide oxidizing composition.

The mixtures obtained are applied to locks of hair at a rate of 5 g of mixture per 1 g of hair at 27° C. for 35 minutes for Majirouge Mix Plus Absolu and 15 minutes for Movida 45. The locks are then washed with a standard shampoo, rinsed and then dried.

II) Stripping Step

The following compositions are prepared.

1) Composition (A): Anhydrous Paste

| | Composition A1 % AM in g | Composition A2 % AM in g |
|---|---|---|
| Bruggolite FF7 (Bruggemann Chemical) | | |
| Disodium salt of hydroxysulfinoacetate acid | 16 | 16 |
| Disodium salt of hydroxysulfoacetate acid | 27.5 | 27.5 |
| Sodium sulfite | 1.5 | 1.5 |
| Fillers | 5 | 5 |
| Calcium stearate | 15 | 15 |
| Hydrogenated polydecene (Silkflo 366 NF Polydecene from Ineos) | 35 | 35 |
| Fumed silica of hydrophilic nature (Cabot Aerosil 300 from Evonik-Degussa) | 1.5 | — |
| Beeswax (White Beeswax from Koster Keunen) | — | 1.5 |

2) Aqueous Composition (B): Acidic Solution of pH 2

|  | Composition B1 % AM in g | Composition B2 % AM in g |
|---|---|---|
| Mixture of cetylstearyl alcohol/30 OE oxyethylenated cetylstearyl alcohol (Sinnowax AO from Cognis) | 3 | 3 |
| (50% linear 70/30 C13/C15)alkyl ether carboxylic acid monoethanolamide (2 OE) (Amidet A15 from Kao) | 1 | — |
| Oxyethylenated (4 OE) rapeseed acid amide (Amidet N from Kao) | — | 1 |
| Glycerol | 0.7 | 0.7 |
| Diethylenetriaminepentaacetic acid, pentasodium salt as a 40% aqueous solution | 0.15 | 0.15 |
| Benzoic acid | 0.20 | 0.20 |
| Tartaric acid powder | 20 | 20 |
| Trisodium phosphate dodecahydrate | 2.5 | 2.5 |
| Fragrance | 1 | 1 |
| Deionized water | qs 100 | qs 100 |

Each of the compositions (A1) or (A2) is mixed with one of the compositions (B1) or (B2) at the time of use in a proportion of 1 part by weight of anhydrous paste per 3 parts by weight of aqueous solution, to obtain four compositions of pH 2.7.

The compositions thus obtained are applied to locks of predyed hair according to the procedure described above, for 40 minutes, on a hotplate at 27° C.

The bath ratio is 10 g of composition per 1 g of hair. After the leave-on time, the locks are washed, rinsed and then dried.

With the four mixtures, very good stripping is obtained on the two types of fibre (natural or permanent-waved grey hair).

EXAMPLES B

I) Dyeing Step 1-g locks of natural, permanent-waved or non-permanent-waved hair containing 90% grey hairs are dyed with Majirouge Mix Plus Absolu Nuance Rouge (L'Oréal Professionnel) or with Movida 45 (Garnier).
Majirouge Mix Plus Absolu Nuance Rouge Dye Composition:
p-phenylenediamine: 0.25 g %
resorcinol: 0.009 g %
p-aminophenol: 0.25 g %
4-amino-2-hydroxybenzene: 0.26 g %
2-methyl-5-hydroxyethylaminophenol: 0.82 g %
Movida 45 Dye Composition:
p-toluenediamine: 1.9 g %
resorcinol: 0.7 g %
2-(β-hydroxyethyloxy)-p-phenylenediamine dihydrochloride: 0.06 g %
m-aminophenol: 0.08 g %
2-methylresorcinol: 1.1 g %

10 g of each of the dye compositions are mixed with 15 g (for Majirouge Mix Plus Absolu Nuance Rouge) or 20 g (for Movida 45) of a 20-volumes hydrogen peroxide oxidizing composition.

The mixtures obtained are applied to locks of hair at a rate of 5 g of mixture per 1 g of hair at 27° C. for 35 minutes for Majirouge Mix Plus Absolu and 15 minutes for Movida 45. The locks are then washed with a standard shampoo, rinsed and then dried.

II) Stripping Step
The following compositions are prepared.
1) Composition (A): Anhydrous Paste

|  | Composition A1 % AM in g | Composition A2 % AM in g |
|---|---|---|
| Bruggolite FF7 (Bruggemann Chemical) | | |
| Disodium salt of hydroxysulfinoacetate acid | 16 | 16 |
| Disodium salt of hydroxysulfoacetate acid | 27.5 | 27.5 |
| Sodium sulfite | 1.5 | 1.5 |
| Fillers | 5 | 5 |
| Calcium stearate | 15 | 15 |
| Xanthan gum (Keltrol CG-BT from CP Kelco) | 4 | 4 |
| Hydrogenated polydecene | 35 | 35 |
| Fumed silica of hydrophilic nature (Aerosil 300) | 1.5 | — |
| Beeswax | — | 1.5 |

2) Aqueous Composition (B): Acidic Solution of pH 2

|  | Composition B1 % AM in g | Composition B2 % AM in g |
|---|---|---|
| Mixture of cetylstearyl alcohol/30 OE oxyethylenated cetylstearyl alcohol (Sinnowax AO from Cognis) | 3 | 3 |
| (50% linear 70/30 $C_{13}/C_{15}$)alkyl ether carboxylic acid monoethanolamide (2 OE) (Amidet A15 from Kao) | 1 | — |
| Oxyethylenated (4 OE) rapeseed acid amide (Amidet N from Kao) | — | 1 |
| Glycerol | 0.7 | 0.7 |
| Diethylenetriaminepentaacetic acid, pentasodium salt as a 40% aqueous solution | 0.15 | 0.15 |
| Benzoic acid | 0.20 | 0.20 |
| Tartaric acid | 20 | 20 |
| Trisodium phosphate dodecahydrate | 2.5 | 2.5 |
| Fragrance | 1 | 1 |
| Water | qs 100 | qs 100 |

Each of the compositions (A1) or (A2) is mixed with one of the compositions (B1) or (B2) at the time of use in a proportion of 1 part by weight of anhydrous paste per 3 parts by weight of aqueous solution, to obtain four compositions of pH 2.7.

The compositions thus obtained are applied to locks of predyed hair according to the procedure described above, for 40 minutes, on a hotplate at 27° C.

The bath ratio is 10 g of composition per 1 g of hair. After the leave-on time, the locks are washed, rinsed and then dried.

With the four mixtures, very good stripping is obtained on the two types of fibre (natural or permanent-waved grey hair).

The invention claimed is:
1. A process for stripping keratin fibers dyed with oxidation dyes and/or direct dyes, said process comprising applying a mixture to the keratin fibers, wherein the mixture is obtained by mixing:
(a) an anhydrous composition (A) comprising:
(i) an inert organic liquid phase, and
(ii) at least one sulfinic acid derivative chosen from compounds of formula (I) or cosmetically acceptable salts thereof:

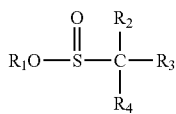

wherein:
R$_1$ is chosen from hydrogen, alkali metal ions, and ionic equivalents of alkaline-earth metals and zinc,
R$_2$ is an OH radical,
R$_3$ is hydrogen, and
R$_4$ is chosen from COOR$_1$; and (b) an aqueous composition (B) with a pH of less than about 5;
wherein the pH of the mixture is less than or equal to about 5; and
wherein the mixture is left on the keratin fibers for a period of time sufficient to strip artificial color from the keratin fibers.

2. The process according to claim 1, wherein the inert organic liquid comprises at least one of: polydecenes of formula C$_{10n}$H$_{[(20n)+2]}$ wherein n ranges from 3 to 9; esters of fatty alcohols or of fatty acids; sugar esters and diesters of C$_{12}$-C$_{24}$ fatty acids; cyclic esters; cyclic ethers; silicone oils; mineral oils; plant oils; or mixtures thereof.

3. The process according to claim 1, wherein the anhydrous composition (A) is a paste.

4. The process according to claim 1, wherein the pH of the aqueous composition (B) is less than about 3.

5. The process according to claim 1, wherein the aqueous composition (B) comprises at least one fatty alcohol chosen from non-(poly)oxyalkylenated alcohols (the alkyl containing 1 to 3 carbon atoms), non-(poly)glycerolated alcohols comprising at least one fatty chains containing from 10 to 30 carbon atoms, which are saturated or unsaturated, the fatty chains being optionally substituted with one or two additional hydroxyl groups, or mixtures thereof.

6. The process according to claim 1, wherein the mixture further comprises at least one thickening polymer chosen from anionic thickening polymers, nonionic thickening polymers, or mixtures thereof.

7. The process according to claim 6, wherein the mixture has a weight ratio of sulfinic acid derivatives of formula (I) or cosmetically acceptable salts thereof to thickening polymers ranging from 0.2 to 20.

8. The process according to claim 1, wherein the mixture comprises a total amount of sulfinic acid derivatives of formula (I) or cosmetically acceptable salts thereof ranging from 0.01% to 20% by weight, relative to the total weight of the mixture.

9. The process according to claim 1, wherein composition (B) further comprises at least one organic acid or salt thereof other than sulfinic acid derivatives of formula (I), wherein the at least one organic acid has a pKa of less than or equal to 4.

10. The process according to claim 9, wherein the at least one organic acid with a pKa of less than or equal to 4 are chosen from α-hydroxy acids with a pKa of less than or equal to 4.

11. The process according to claim 9, wherein the mixture has a weight ratio of the sulfinic acid derivatives of formula (I) or cosmetically acceptable salts thereof to organic acids having a pKa of less than or equal to 4 or salts thereof ranging from 0.1 to 5.

12. The process according to claim 1, wherein compositions (A) and (B) are mixed in a weight ratio of (A):(B) ranging from 0.1 to 10.

13. A process for stripping keratin fibers dyed with oxidation dyes and/or direct dyes, said process comprising applying a mixture to the keratin fibers, wherein the mixture is obtained by mixing:

(a) an anhydrous composition (A) comprising:
(i) an inert organic liquid phase, and
(ii) a sulfinic acid derivative of formula (II):

and (b) an aqueous composition (B) with a pH of less than about 5;
wherein the pH of the mixture is less than or equal to about 5; and
wherein the mixture is left on the keratin fibers for a period of time sufficient to strip artificial color from the keratin fibers.

14. The process according to claim 13, wherein the inert organic liquid phase comprises at least one of: polydecenes of formula C$_{10n}$H$_{[(20n)+2]}$, wherein n ranges from 3 to 9; esters of fatty alcohols or of fatty acids; sugar esters and diesters of C$_{12}$-C$_{24}$ fatty acids; cyclic esters; cyclic ethers; silicone oils; mineral oils; plant oils; or mixtures thereof.

15. The process according to claim 13, wherein the anhydrous composition (A) is a paste.

16. The process according to claim 13, wherein the pH of the aqueous composition (B) is less than about 3.

17. The process according to claim 13, wherein the aqueous composition (B) comprises at least one fatty alcohol chosen from non-(poly)oxyalkylenated alcohols (the alkyl containing 1 to 3 carbon atoms), non-(poly)glycerolated alcohols comprising at least one fatty chain containing from 10 to 30 carbon atoms, which are saturated or unsaturated, the at least one fatty chain being optionally substituted with one or two additional hydroxyl groups, or mixtures thereof.

18. The process according to claim 13, wherein the mixture further comprises at least one thickening polymer chosen from anionic thickening polymers, nonionic thickening polymers, or mixtures thereof.

19. The process according to claim 18, wherein the mixture has a weight ratio of the sulfinic acid derivative of formula (II) to thickening polymers ranging from 2 to 15.

20. The process according to claim 13, wherein the mixture comprises from 0.01% to 20% of the sulfinic acid derivative of formula (II) by weight, relative to the total weight of the mixture.

21. The process according to claim 13, wherein composition (B) comprises at least one organic acid or salt thereof other than the sulfinic acid derivative of formula (II), wherein the organic acid has a pKa of less than or equal to 4.

22. The process according to claim 21, wherein the mixture has a weight ratio of sulfinic acid derivative of formula (II) to organic acids having a pKa of less than or equal to 4 or salts thereof ranging from 0.2 to 1.5.

23. The process according to claim 13, wherein compositions (A) and (B) are mixed in a weight ratio of (A):(B) ranging from 0.2 to 4.

\* \* \* \* \*